United States Patent
Myers, III et al.

(10) Patent No.: US 11,465,142 B2
(45) Date of Patent: *Oct. 11, 2022

(54) MULTIPLEXED BIOLOGICAL ASSAY DEVICE WITH ELECTRONIC READOUT

(71) Applicant: Lucira Health, Inc., Emeryville, CA (US)

(72) Inventors: Frank B. Myers, III, Richmond, CA (US); Clay D. Reber, Berkeley, CA (US); Taber H. Smith, Saratoga, CA (US); Faisal S. Maniar, San Jose, CA (US)

(73) Assignee: Lucira Health, Inc., Emeryville, CA (US)

( * ) Notice: Subject to any disclaimer, the term of this patent is extended or adjusted under 35 U.S.C. 154(b) by 362 days.

This patent is subject to a terminal disclaimer.

(21) Appl. No.: 16/722,475

(22) Filed: Dec. 20, 2019

(65) Prior Publication Data

US 2020/0122142 A1    Apr. 23, 2020

Related U.S. Application Data

(63) Continuation of application No. 16/185,314, filed on Nov. 9, 2018, now Pat. No. 10,549,275, which is a
(Continued)

(51) Int. Cl.
*B01L 3/00* (2006.01)
*G01N 21/78* (2006.01)
(Continued)

(52) U.S. Cl.
CPC ........... *B01L 3/502715* (2013.01); *B01L 7/52* (2013.01); *C12Q 1/6844* (2013.01);
(Continued)

(58) Field of Classification Search
CPC ............... B01L 7/52; B01L 2200/027; B01L 2200/0684; B01L 2200/0689;
(Continued)

(56) References Cited

U.S. PATENT DOCUMENTS

| D244,555 S | 5/1977 | Wiedmann |
| 4,310,488 A | 1/1982 | Rahm et al. |

(Continued)

FOREIGN PATENT DOCUMENTS

| AU | 2003272465 A1 | 10/2004 |
| CA | 2495252 A1 | 3/2004 |

(Continued)

OTHER PUBLICATIONS

Canadian Office Action for Application No. 2,944,994, dated Aug. 8, 2019, 3 pages.
(Continued)

*Primary Examiner* — Dennis White
(74) *Attorney, Agent, or Firm* — Goodwin Procter LLP

(57) ABSTRACT

This invention relates generally to devices, systems, and methods for performing biological assays by using indicators that modify one or more optical properties of the assayed biological samples. The subject methods include generating a reaction product by carrying out a biochemical reaction on the biological sample introduced into a device and reacting the reaction product with an indicator capable of generating a detectable change in an optical property of the biological sample to indicate the presence, absence, or amount of analyte suspected to be present in the sample.

64 Claims, 14 Drawing Sheets

Related U.S. Application Data continuation of application No. PCT/US2018/044044, filed on Jul. 27, 2018.

(60) Provisional application No. 62/558,815, filed on Sep. 14, 2017.

(51) Int. Cl.

| | | |
|---|---|---|
| *C12Q 1/6844* | (2018.01) | |
| *G01N 21/77* | (2006.01) | |
| *G01N 21/25* | (2006.01) | |
| *G01N 21/03* | (2006.01) | |
| *B01L 7/00* | (2006.01) | |
| *G01N 35/00* | (2006.01) | |
| *G01N 21/27* | (2006.01) | |
| *G01N 35/04* | (2006.01) | |

(52) U.S. Cl.
CPC ....... *G01N 21/0303* (2013.01); *G01N 21/253* (2013.01); *G01N 21/272* (2013.01); *G01N 21/77* (2013.01); *G01N 21/78* (2013.01); *G01N 35/00* (2013.01); *B01L 2200/027* (2013.01); *B01L 2200/0684* (2013.01); *B01L 2200/0689* (2013.01); *B01L 2300/025* (2013.01); *B01L 2300/0654* (2013.01); *B01L 2300/0803* (2013.01); *B01L 2300/0864* (2013.01); *B01L 2300/1805* (2013.01); *G01N 2035/0436* (2013.01); *G01N 2201/0626* (2013.01)

(58) Field of Classification Search
CPC ....... B01L 2300/025; B01L 2300/0654; B01L 2300/0803; B01L 2300/0864; B01L 2300/1805; B01L 3/502715; C12Q 1/6844; G01N 21/0303; G01N 21/253; G01N 21/272; G01N 21/77; G01N 21/78; G01N 35/00; G01N 2035/0436; G01N 2201/0626
See application file for complete search history.

(56) References Cited

U.S. PATENT DOCUMENTS

| | | | |
|---|---|---|---|
| 4,379,848 A | 4/1983 | Yeaw | |
| 4,624,929 A | 11/1986 | Ullman | |
| 4,849,340 A | 7/1989 | Oberhardt | |
| 4,859,610 A | 8/1989 | Maggio | |
| 4,936,682 A | 6/1990 | Hoyt | |
| D334,065 S | 3/1993 | Collister | |
| D371,605 S | 7/1996 | Wong et al. | |
| 5,580,794 A | 12/1996 | Allen | |
| 5,801,062 A | 9/1998 | Sarstedt et al. | |
| 5,830,714 A | 11/1998 | Swaminathan et al. | |
| 5,837,546 A | 11/1998 | Allen et al. | |
| 5,888,826 A | 3/1999 | Ostgaard et al. | |
| 5,958,349 A | 9/1999 | Petersen et al. | |
| 6,071,394 A | 6/2000 | Cheng et al. | |
| 6,074,606 A | 6/2000 | Sayles | |
| 6,180,395 B1 | 1/2001 | Skiffington et al. | |
| 6,198,107 B1 | 3/2001 | Seville | |
| 6,300,142 B1 | 10/2001 | Andrewes et al. | |
| 6,336,900 B1 | 1/2002 | Alleckson et al. | |
| 6,352,838 B1 | 3/2002 | Krulevitch et al. | |
| D456,082 S | 4/2002 | Bouse et al. | |
| 6,564,968 B1 | 5/2003 | Terrell et al. | |
| 6,565,808 B2 | 5/2003 | Hudak et al. | |
| 6,699,384 B1 | 3/2004 | Lin et al. | |
| 6,817,256 B2 | 11/2004 | Mehra et al. | |
| 6,900,059 B1 | 5/2005 | Shinn et al. | |
| D507,351 S | 7/2005 | Birnboim | |
| 7,156,809 B2 | 1/2007 | Quy | |
| 7,256,035 B1 | 8/2007 | Schnell et al. | |
| D559,996 S | 1/2008 | Okamoto et al. | |
| D560,812 S | 1/2008 | Powell et al. | |
| D561,905 S | 2/2008 | Ramel et al. | |
| D567,961 S | 4/2008 | Yajima | |
| D574,507 S | 8/2008 | Muir et al. | |
| 7,438,852 B2 | 10/2008 | Tung et al. | |
| 7,452,667 B2 | 11/2008 | Liew et al. | |
| D602,599 S | 10/2009 | Xiaowei | |
| D608,885 S | 1/2010 | Sneddon et al. | |
| D618,351 S | 6/2010 | Hara | |
| 7,850,922 B2 | 12/2010 | Gallagher et al. | |
| D631,553 S | 1/2011 | Niedbala et al. | |
| D659,848 S | 5/2012 | TerMaat et al. | |
| D669,375 S | 10/2012 | Kao et al. | |
| D675,335 S | 1/2013 | Feuerabend et al. | |
| 8,372,353 B2 | 2/2013 | Lee et al. | |
| D683,642 S | 6/2013 | Buesser et al. | |
| D686,311 S | 7/2013 | Mori | |
| D687,564 S | 8/2013 | Yang et al. | |
| 8,719,989 B1 | 5/2014 | Qanaei | |
| 9,034,606 B2 | 5/2015 | Tanner et al. | |
| 9,074,243 B2 | 7/2015 | Tanner et al. | |
| 9,074,249 B2 | 7/2015 | Tanner et al. | |
| D736,403 S | 8/2015 | Hudson et al. | |
| D743,571 S | 11/2015 | Jackson | |
| D748,813 S | 2/2016 | Ishiguro et al. | |
| D749,420 S | 2/2016 | Maggio | |
| 9,278,321 B2 | 3/2016 | Dale et al. | |
| D773,069 S | 11/2016 | Curry | |
| 9,546,358 B2 | 1/2017 | Tanner et al. | |
| D787,682 S | 5/2017 | Ockham et al. | |
| D791,952 S | 7/2017 | Florescu et al. | |
| 9,739,743 B2 | 8/2017 | Athanasiou et al. | |
| D800,912 S | 10/2017 | Uzri et al. | |
| 9,815,061 B2 | 11/2017 | Delattre et al. | |
| D808,833 S | 1/2018 | Abbott et al. | |
| D820,130 S | 6/2018 | Khattak et al. | |
| D821,602 S | 6/2018 | Sever et al. | |
| 9,999,889 B2 | 6/2018 | Khattak et al. | |
| D825,772 S | 8/2018 | Sever et al. | |
| D829,336 S | 9/2018 | Wohlstadter et al. | |
| D829,337 S | 9/2018 | Klein et al. | |
| 10,093,965 B2 | 10/2018 | Toumazou et al. | |
| 10,146,909 B2 | 12/2018 | Dimov et al. | |
| D838,379 S | 1/2019 | Trump | |
| D840,049 S | 2/2019 | Schulz et al. | |
| 10,195,606 B2 | 2/2019 | Khattak et al. | |
| 10,253,357 B2 | 4/2019 | Mitra et al. | |
| 10,272,434 B2 | 4/2019 | Khattak et al. | |
| D854,703 S | 7/2019 | Juhlin et al. | |
| D855,212 S | 7/2019 | Komuro | |
| 10,343,160 B2 | 7/2019 | Lemoine et al. | |
| D859,683 S | 9/2019 | Harding et al. | |
| D860,472 S | 9/2019 | Blake et al. | |
| D865,212 S | 10/2019 | Kakuda et al. | |
| D865,218 S | 10/2019 | Mathers et al. | |
| 10,449,538 B1 | 10/2019 | Carrano et al. | |
| D867,584 S | 11/2019 | Zercher et al. | |
| D869,311 S | 12/2019 | Khattak et al. | |
| 10,545,161 B2 | 1/2020 | Khattak et al. | |
| D874,677 S | 2/2020 | Stamm et al. | |
| D875,963 S | 2/2020 | Gruen | |
| 10,549,275 B2 | 2/2020 | Myers, III et al. | |
| D879,319 S | 3/2020 | Kakuda et al. | |
| D879,320 S | 3/2020 | Kakuda et al. | |
| D879,994 S | 3/2020 | Leimkuehler et al. | |
| 10,589,267 B2 | 3/2020 | Khattak et al. | |
| 10,603,664 B2 | 3/2020 | Khattak et al. | |
| D882,110 S | 4/2020 | Klein et al. | |
| D883,515 S | 5/2020 | Jenoski et al. | |
| D886,901 S | 6/2020 | Hussey et al. | |
| 10,843,185 B2 | 11/2020 | Gorin et al. | |
| D907,232 S | 1/2021 | Reber et al. | |
| D923,797 S | 6/2021 | Parks et al. | |
| D928,341 S | 8/2021 | Thimm et al. | |
| 2001/0012612 A1 | 8/2001 | Petersen et al. | |
| 2002/0001539 A1 | 1/2002 | DiCesare et al. | |
| 2002/0039783 A1 | 4/2002 | McMillan et al. | |
| 2002/0042125 A1 | 4/2002 | Petersen et al. | |

(56) References Cited

U.S. PATENT DOCUMENTS

| | | |
|---|---|---|
| 2003/0064526 A1 | 4/2003 | Niedbala et al. |
| 2003/0123994 A1 | 7/2003 | Weng et al. |
| 2003/0157503 A1 | 8/2003 | McGarry et al. |
| 2004/0018634 A1 | 1/2004 | Hajizadeh et al. |
| 2004/0052689 A1 | 3/2004 | Yao |
| 2004/0118189 A1 | 6/2004 | Karp et al. |
| 2004/0166569 A1 | 8/2004 | Marziali et al. |
| 2004/0203174 A1 | 10/2004 | Jones et al. |
| 2004/0208792 A1 | 10/2004 | Linton et al. |
| 2004/0209275 A1 | 10/2004 | Liew et al. |
| 2005/0022895 A1 | 2/2005 | Barth et al. |
| 2005/0221281 A1 | 10/2005 | Ho |
| 2006/0078929 A1 | 4/2006 | Bickel et al. |
| 2006/0094004 A1* | 5/2006 | Nakajima ......... B01L 3/502761 435/5 |
| 2006/0166354 A1 | 7/2006 | Wikswo et al. |
| 2006/0194207 A1 | 8/2006 | Mitani et al. |
| 2006/0245977 A1 | 11/2006 | Bodner |
| 2007/0014695 A1 | 1/2007 | Yue et al. |
| 2007/0166200 A1 | 7/2007 | Zhou et al. |
| 2007/0183934 A1 | 8/2007 | Diercks et al. |
| 2007/0217963 A1 | 9/2007 | Elizarov et al. |
| 2008/0000892 A1 | 1/2008 | Hirano et al. |
| 2008/0038713 A1 | 2/2008 | Gao et al. |
| 2008/0056948 A1 | 3/2008 | Dale et al. |
| 2008/0149840 A1 | 6/2008 | Handique et al. |
| 2008/0204380 A1 | 8/2008 | Shin et al. |
| 2008/0233015 A1 | 9/2008 | Turner |
| 2009/0004732 A1 | 1/2009 | LaBarre et al. |
| 2009/0048115 A1 | 2/2009 | Liew et al. |
| 2009/0071911 A1 | 3/2009 | Folden et al. |
| 2009/0151864 A1 | 6/2009 | Burke et al. |
| 2009/0203973 A1 | 8/2009 | Donoghue et al. |
| 2009/0305315 A1 | 12/2009 | Gandola et al. |
| 2009/0308185 A1 | 12/2009 | Wu et al. |
| 2009/0320684 A1 | 12/2009 | Weaver et al. |
| 2010/0015611 A1 | 1/2010 | Webster et al. |
| 2010/0229956 A1 | 9/2010 | Luyendijk |
| 2010/0323919 A1 | 12/2010 | Chen et al. |
| 2010/0331219 A1 | 12/2010 | Munenaka |
| 2011/0003330 A1 | 1/2011 | Durack |
| 2011/0005932 A1 | 1/2011 | Jovanovich et al. |
| 2011/0124098 A1 | 5/2011 | Rose et al. |
| 2011/0151432 A1 | 6/2011 | Zappia et al. |
| 2011/0294112 A1 | 12/2011 | Bearinger et al. |
| 2011/0294205 A1 | 12/2011 | Hukari et al. |
| 2012/0040445 A1 | 2/2012 | Bouma et al. |
| 2012/0100624 A1 | 4/2012 | Hara et al. |
| 2012/0105837 A1 | 5/2012 | Ingber |
| 2012/0285562 A1 | 11/2012 | Richardson |
| 2013/0003162 A1 | 1/2013 | Leoni et al. |
| 2013/0130232 A1 | 5/2013 | Weibel et al. |
| 2013/0244241 A1 | 9/2013 | Carrera Fabra et al. |
| 2013/0266948 A1 | 10/2013 | Bird et al. |
| 2013/0280725 A1 | 10/2013 | Ismagilov et al. |
| 2013/0295663 A1 | 11/2013 | Weight et al. |
| 2013/0323738 A1 | 12/2013 | Tanner et al. |
| 2013/0323793 A1 | 12/2013 | Tanner et al. |
| 2014/0031248 A1 | 1/2014 | Tanner et al. |
| 2014/0057210 A1 | 2/2014 | Malik et al. |
| 2014/0057268 A1 | 2/2014 | Tanner et al. |
| 2014/0073013 A1 | 3/2014 | Gorman et al. |
| 2014/0073043 A1 | 3/2014 | Holmes |
| 2014/0170661 A1 | 6/2014 | Lamura et al. |
| 2014/0188089 A1 | 7/2014 | Midgette et al. |
| 2014/0228773 A1 | 8/2014 | Burkholz |
| 2014/0242612 A1 | 8/2014 | Wang et al. |
| 2014/0335505 A1 | 11/2014 | Holmes |
| 2014/0356874 A1 | 12/2014 | Bearinger |
| 2015/0024436 A1 | 1/2015 | Eberhart et al. |
| 2015/0111201 A1 | 4/2015 | Ozcan et al. |
| 2015/0132795 A1 | 5/2015 | Griswold et al. |
| 2015/0151300 A1 | 6/2015 | Williams et al. |
| 2015/0154449 A1 | 6/2015 | Ito et al. |
| 2015/0182966 A1 | 7/2015 | Coursey |
| 2015/0240293 A1 | 8/2015 | Tanner et al. |
| 2015/0247190 A1 | 9/2015 | Ismagilov et al. |
| 2015/0298118 A1 | 10/2015 | Chard et al. |
| 2015/0321193 A1 | 11/2015 | Sprague et al. |
| 2015/0328638 A1 | 11/2015 | Handique et al. |
| 2015/0359458 A1 | 12/2015 | Erickson et al. |
| 2016/0077015 A1 | 3/2016 | Holmes et al. |
| 2016/0194685 A1 | 7/2016 | Unger et al. |
| 2016/0216287 A1 | 7/2016 | Holmes et al. |
| 2016/0275149 A1 | 9/2016 | Majumdar et al. |
| 2016/0334403 A1 | 11/2016 | Gibbons et al. |
| 2017/0044599 A1 | 2/2017 | Mitra et al. |
| 2018/0293350 A1 | 10/2018 | Dimov et al. |
| 2018/0372595 A1 | 12/2018 | Pais et al. |
| 2019/0050988 A1 | 2/2019 | Dimov et al. |
| 2019/0060895 A1 | 2/2019 | Myers, III et al. |
| 2019/0076841 A1 | 3/2019 | Myers, III et al. |
| 2019/0083975 A1 | 3/2019 | Mitra et al. |
| 2019/0094114 A1 | 3/2019 | Myers, III et al. |
| 2019/0309356 A1 | 10/2019 | Mitra et al. |
| 2019/0314810 A1 | 10/2019 | Khattak et al. |
| 2020/0030798 A1 | 1/2020 | Mitra et al. |
| 2020/0164373 A1 | 5/2020 | Khattak et al. |
| 2020/0290035 A1 | 9/2020 | Samsoondar |
| 2020/0323474 A1 | 10/2020 | McIntosh |
| 2021/0378643 A1 | 12/2021 | Roswech et al. |

FOREIGN PATENT DOCUMENTS

| | | |
|---|---|---|
| CN | 104937108 A | 9/2015 |
| CN | 105441312 A | 3/2016 |
| CN | 201930535293.7 | 4/2020 |
| EP | 0056241 A1 | 7/1981 |
| EP | 0520408 A2 | 12/1992 |
| EP | 1557673 A1 | 7/2005 |
| EP | 1581652 A2 | 10/2005 |
| EP | 1661988 A1 | 5/2006 |
| EP | 2251435 B1 | 10/2013 |
| EP | 2888374 A1 | 7/2015 |
| IN | 287440 | 8/2019 |
| JP | 62-151198 A | 7/1987 |
| JP | 2006506979 A | 3/2006 |
| JP | 2008-173218 A | 7/2008 |
| JP | 2010-061383 A | 3/2010 |
| JP | 2010-538801 A | 12/2010 |
| JP | 2013-526867 A | 6/2013 |
| JP | 2013-532488 A | 8/2013 |
| JP | 2013-228350 A | 11/2013 |
| JP | 2015532593 A | 11/2015 |
| WO | 1997/011723 A1 | 4/1997 |
| WO | 9712681 A1 | 4/1997 |
| WO | WO 1997/041421 A1 | 11/1997 |
| WO | WO 2004/024892 A2 | 3/2004 |
| WO | 2005/012518 A1 | 2/2005 |
| WO | WO 2008/107014 A1 | 9/2008 |
| WO | 2009/033178 A1 | 3/2009 |
| WO | 2009/039259 A1 | 3/2009 |
| WO | 2009/125227 A1 | 10/2009 |
| WO | 2010/091080 A2 | 8/2010 |
| WO | 2010/132453 A2 | 11/2010 |
| WO | WO 2011/110873 A1 | 9/2011 |
| WO | 2011/123064 A1 | 10/2011 |
| WO | 2011/144345 A1 | 11/2011 |
| WO | 2012/018741 A2 | 2/2012 |
| WO | WO 2012/045889 A | 4/2012 |
| WO | WO 2013/008042 A1 | 1/2013 |
| WO | 2013/080154 A1 | 6/2013 |
| WO | WO 2014/018828 A1 | 1/2014 |
| WO | 2014/019829 A1 | 2/2014 |
| WO | 2014/020326 A2 | 2/2014 |
| WO | WO 2014/031783 A1 | 2/2014 |
| WO | 2014/144548 A2 | 9/2014 |
| WO | 2015/037281 A1 | 3/2015 |
| WO | 2015164770 A1 | 10/2015 |
| WO | 2015/184360 A1 | 12/2015 |
| WO | 2017/160836 A1 | 9/2017 |
| WO | 2017/160838 A1 | 9/2017 |
| WO | 2017/160839 A1 | 9/2017 |
| WO | 2017/160840 A1 | 9/2017 |

(56) References Cited

FOREIGN PATENT DOCUMENTS

| WO | 2018140540 A1 | 8/2018 |
|---|---|---|
| WO | 2018/185573 A1 | 10/2018 |
| WO | 2019/055135 A1 | 3/2019 |
| WO | 2020/180858 A1 | 9/2020 |

OTHER PUBLICATIONS

European Application No. 17767336.5, Extended European Search Report dated Sep. 26, 2019, 14 pages.
European Application No. 17767337.3, Extended European Search Report dated Sep. 18, 2019, 6 pages.
European Application No. 17767339.9, Extended European Search Report dated Oct. 4, 2019, 11 pages.
European Search Report for European Patent Application No. EP 19178796.9, dated Oct. 9, 2019, 7 Pages.
Goto., M., et al., "Colorimetric detection of loop-mediated isothermal amplification reaction by using hydroxy naphthol blue", Biotechniques, Mar. 1, 2009, pp. 167-172, vol. 46, No. 3.
Non-Final Office Action for U.S. Appl. No. 15/306,240, dated Jul. 24, 2018, 8 pages.
Non-Final Office Action for U.S. Appl. No. 16/359,913, dated Oct. 1, 2019, 9 pages.
Non-Final Office Action for U.S. Appl. No. 29/674,581, dated Jan. 8, 2020, 11 pages.
Partial Supplemental European Search Report for European Patent Application No. EP 17767338.1, dated Oct. 10, 2019, 15 Pages.
Patent Cooperation Treaty, International Search Report and Written Opinion of the International Searching Authority, International Patent Application No. PCT/US19/55365, dated Feb. 5, 2020, 20 Pages.
Patent Cooperation Treaty, International Search Report and Written Opinion of the International Searching Authority, International Patent Application No. PCT/US2015/027556, dated Sep. 15, 2015, 18 Pages.
Patent Cooperation Treaty, International Search Report and Written Opinion of the International Searching Authority, International Patent Application No. PCT/US2017/022300, dated Jul. 10, 2017, 15 Pages.
Patent Cooperation Treaty, International Search Report and Written Opinion of the International Searching Authority, International Patent Application No. PCT/US2017/022304, dated Jul. 25, 2017, 20 Pages.
Patent Cooperation Treaty, International Search Report and Written Opinion of the International Searching Authority, International Patent Application No. PCT/US2017/022305, dated Jul. 19, 2017, 20 Pages.
Patent Cooperation Treaty, International Search Report and Written Opinion of the International Searching Authority, International Patent Application No. PCT/US2017/022306, dated Jun. 5, 2017, 18 Pages.
PCT International Search Report and Written Opinion for PCT/IB2018/051326, dated Jun. 26, 2018, 15 pages.
Supplementary European Search Report for European Patent Application No. EP 15783787, dated Nov. 28, 2017, 8 Pages.
Supplementary European Search Report for European Patent Application No. EP 17767338.1, dated Jan. 10, 2020, 13 Pages.
Westcott, S.L., et al., "Broadband optical absorbance spectroscopy using a whispering gallery mode microsphere resonator," Review of Scientific Instruments, vol. 79, No. 3, Mar. 13, 2008, 9 Pages.
PCT International Search Report and Written Opinion for PCT/US2018/044044, dated Sep. 26, 2018, 13 Pages.
Anonymous: "Image Enhancement and Verification Tools—ABBYY Mobile Imaging SDK," Jul. 13, 2014, 12 pages.
Cao et al., "Microfluidic Chip for Molecular Amplication of Influenza A RNA in Human Respiratory Specimens," PLoS One, Mar. 2012, vol. 7, Issue 3, pp. 1-11.
European Search Report, International Application No. EP 18780624, dated Dec. 4, 2020, 10 pages.
Extended European Search Report, European Published Application No. 18857052, dated May 11, 2021, 10 pages.
FDA Approves in-home, rapid results COVID-19 test. Online, published Nov. 18, 2020.
Foo et al., "Rapid Tests for the Diagnosis of Influenza," Australian Prescriber, vol. 32, No. 3, Jun. 2009, pp. 64-67.
Notification of Transmittal of the International Search Report and the Written Opinion of the International Searching Authority, of the Declaration, Int'l Application No. PCT/2021/049178, dated Jan. 14, 2022, 20 pages.
Notification of Transmittal of the International Search Report and the Written Opinion of the International Searching Authority, or the Declaration, Int'l Application No. PCT/US20/20772, dated Jun. 10, 2020, 15 pages.

* cited by examiner

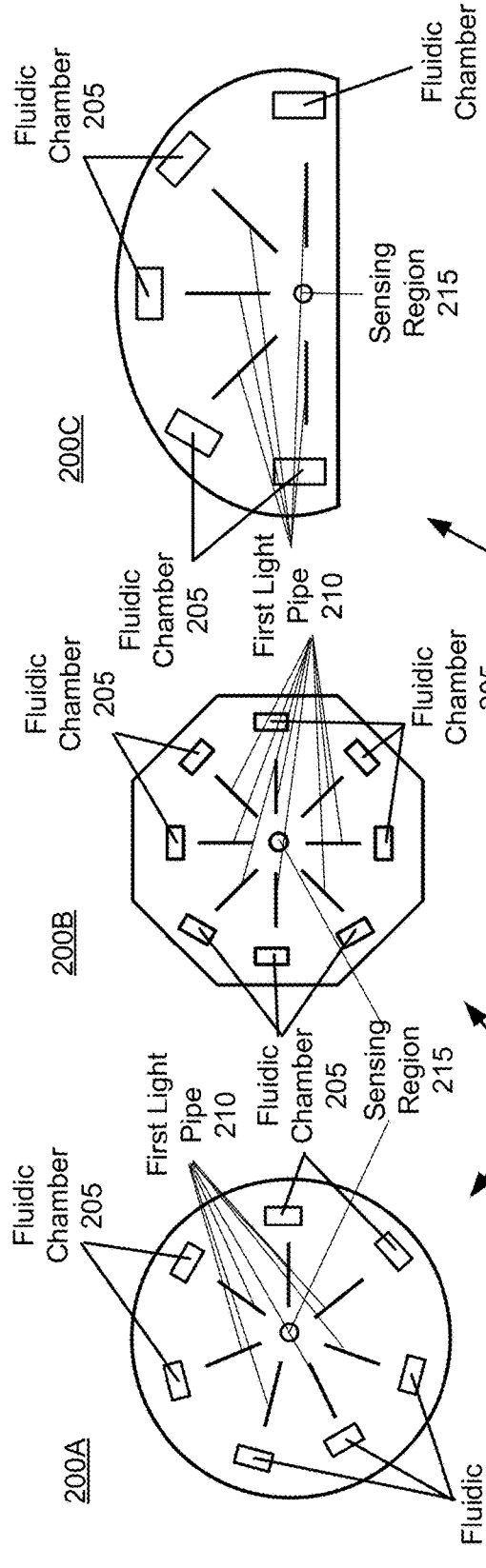
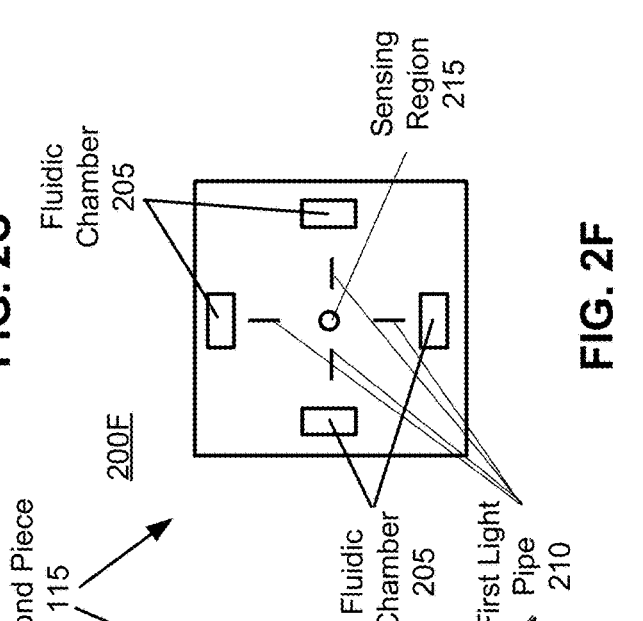
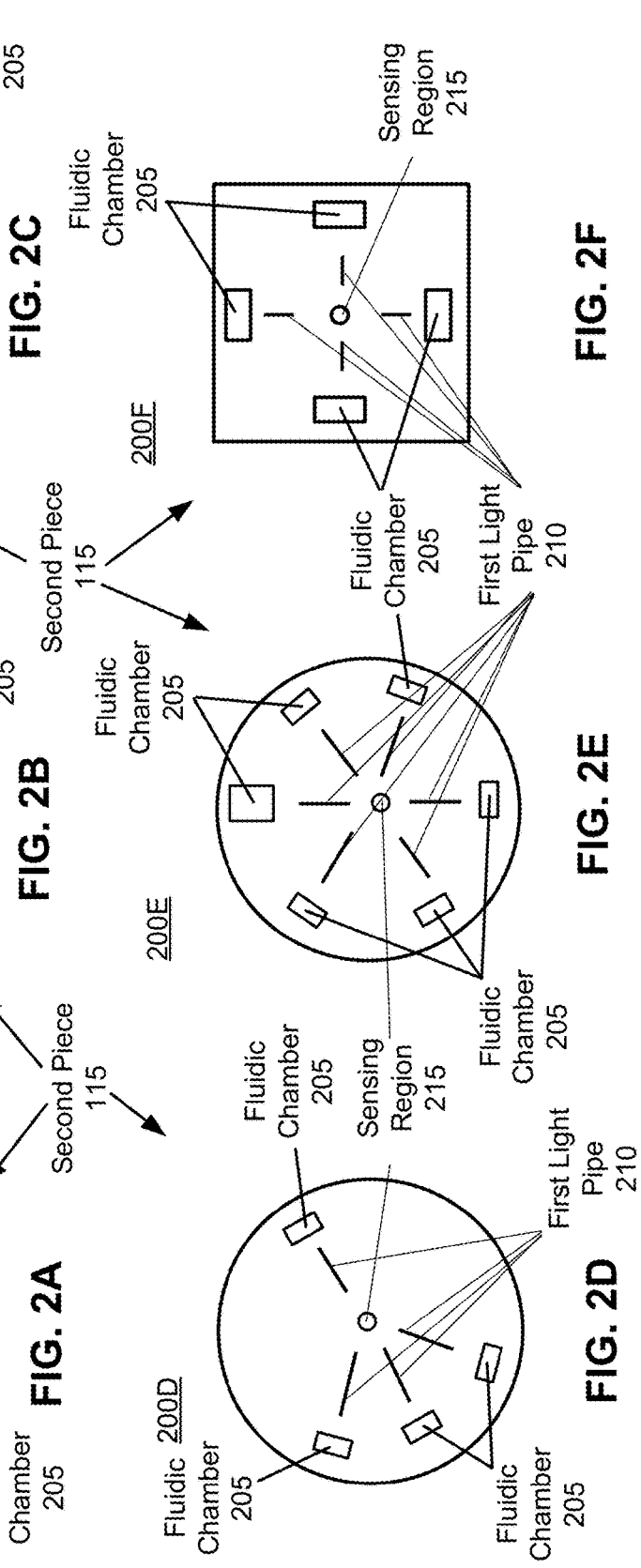
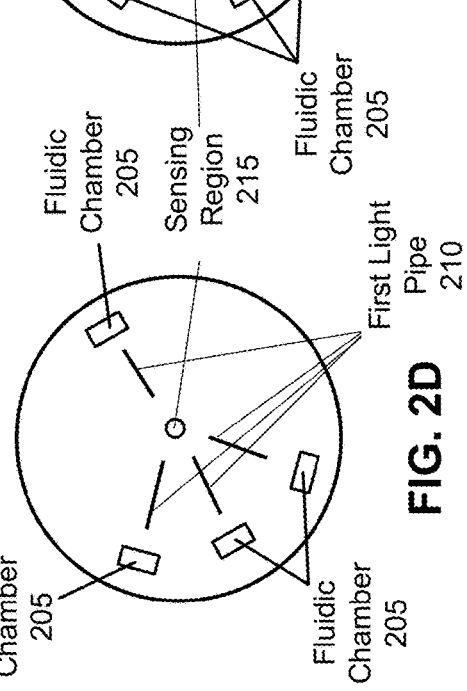

300A
300B
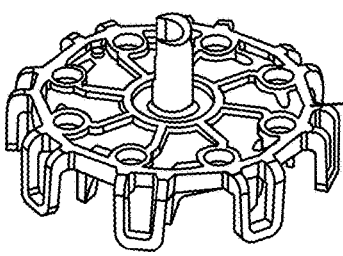 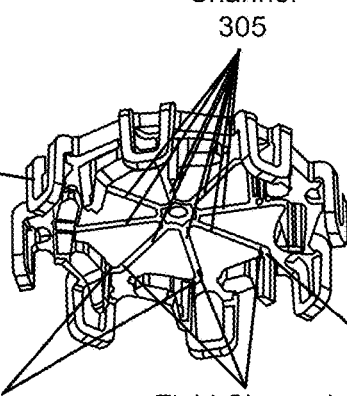
Fluid Channel 305
First Piece 110
Fluidic Chamber Fluid Inlet 315
Fluid Channel Terminus 310
Fluidic Chamber Fluid Inlet 315
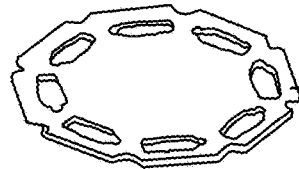 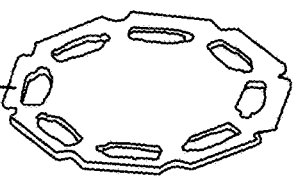
Gasket 320
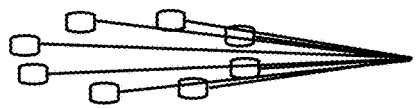 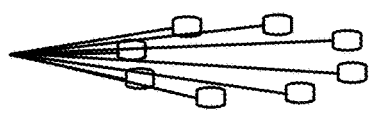
Lyophilized Reagents 330
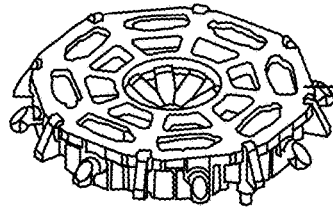 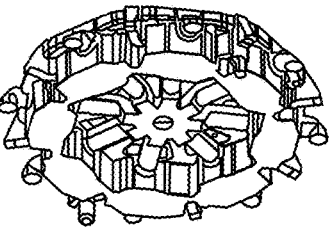
Second Piece 115
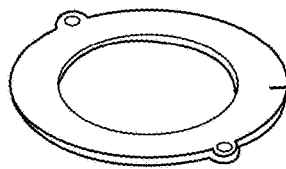 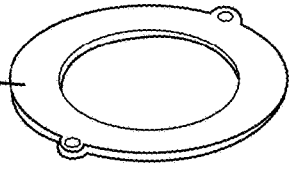
Thermal Pad 325
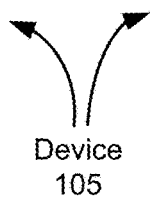
Device 105
FIG. 3A    FIG. 3B

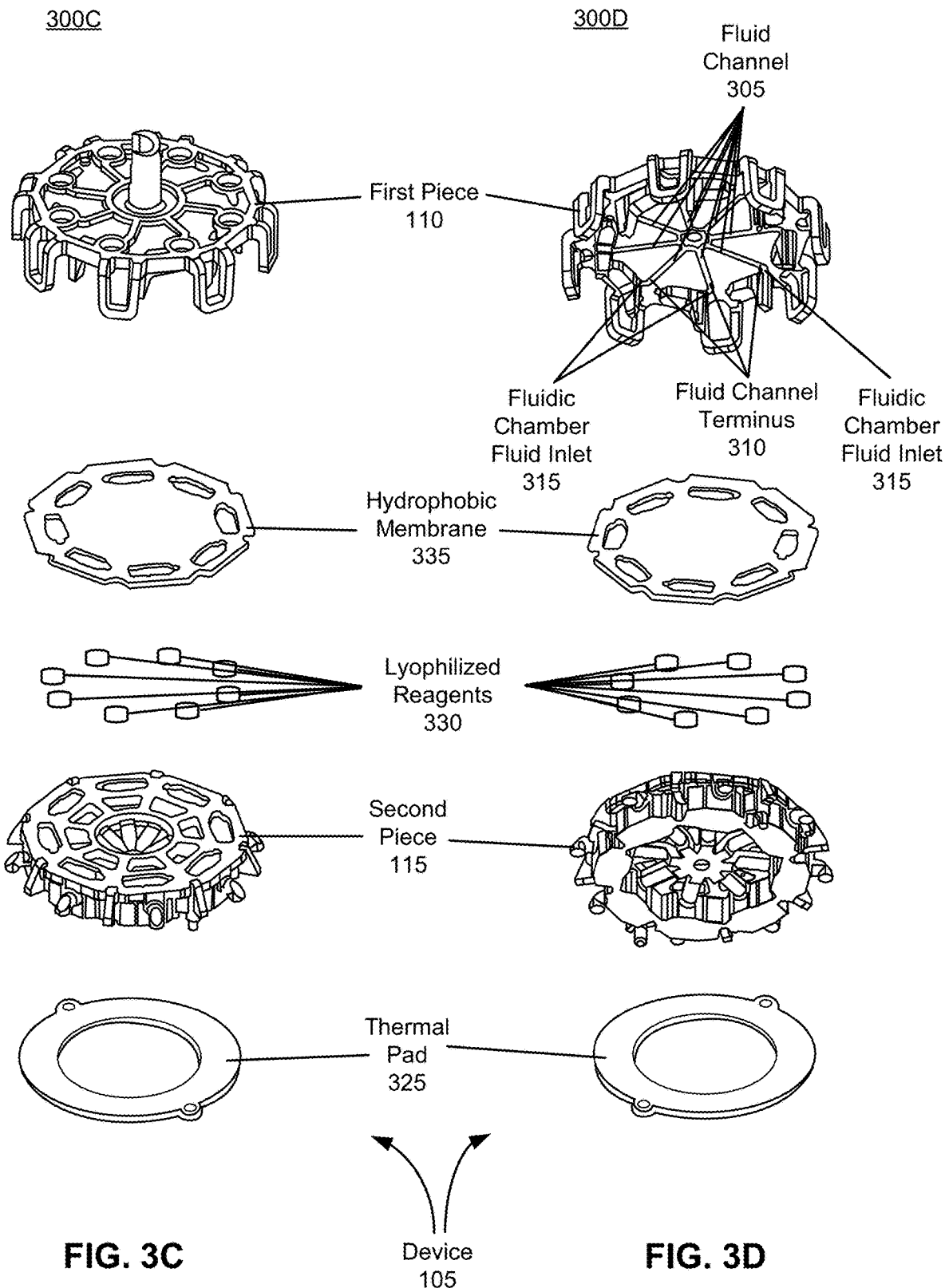

MULTIPLEXED BIOLOGICAL ASSAY DEVICE WITH ELECTRONIC READOUT

CROSS REFERENCE TO RELATED APPLICATION

This application is a continuation of U.S. patent application Ser. No. 16/185,314, filed Nov. 9, 2018, which is a U.S. bypass continuation application of International Application No. PCT/US2018/044044, filed on Jul. 27, 2018, which claims the benefit of U.S. Provisional Application No. 62/558,815, filed on Sep. 14, 2017, all of which are hereby incorporated by reference in their entirety.

INTRODUCTION

Biological assays are used to determine one or more characteristics of biological samples. Such assays can qualitatively assess and/or quantitatively measure the presence, amount and/or functional activity of one or more analytes in a biological sample. Such an assessment can be made based on a change or lack of a change occurring in the assay. For example, a change in transmittance and/or color of an indicator following an assay reaction run on a biological sample indicates one or more characteristics of the sample being evaluated such as the presence, absence, or amount of an analyte suspected to be present in the sample.

BACKGROUND

Most biological assay systems rely on expensive instrumentation for analysis. Very often, this analysis involves detecting changes in optical properties, such as absorbance or fluorescence, within reaction volumes over time. These optical property signals are then analyzed and a determination is made about an analyte within a biological sample often for health monitoring or disease diagnosis. As healthcare costs increase, there is substantial interest in developing low-cost diagnostic devices that can be used outside of traditional laboratory settings, e.g. point-of-care clinics, pharmacies, or in the home. Furthermore, many biological assays chemistries have become available that simplify sample preparation workflows (e.g. eliminating purification requirements) and result analysis (e.g. by relying on colorimetric analysis), making them ideal for these settings. However, a key challenge remains in the design of low-cost instrumentation to enable accurate measurement of optical changes in reaction volumes while simultaneously regulating reaction temperature.

SUMMARY

This disclosed subject matter relates generally to devices and systems for performing biological assays using indicators that modify one or more optical properties of the assayed biological samples. The subject methods include generating a reaction product by carrying out a biochemical reaction on the sample introduced into a device and reacting the reaction product with an indicator capable of generating a detectable change in an optical property of the sample to indicate the presence, absence, or amount of analyte suspected to be present in the sample.

In one aspect, the disclosure provides an assembly for performing a biological assay. In some embodiments, the assembly comprises a first piece comprising a first face and a second piece comprising a second face. The first piece and the second piece can be operatively coupled to create a plurality of independent, continuous fluidic pathways. In certain embodiments, the continuous fluidic pathways comprise a common sample receiving inlet, a plurality of fluid channels, and a plurality of fluidic chambers. In further embodiments, each fluidic chamber of the plurality of fluidic chambers can be substantially equidistant from a single sensing region. As used herein, "substantially equidistant" means that a distance of each fluidic chamber of the plurality of fluidic chambers from the single sensing region, differs from a distance of each other fluidic chamber of the plurality of fluidic chambers from the single sensing region by no more than +/−25%. In some aspects, the plurality of fluid channels can extend from and can be in fluidic communication with the common sample receiving inlet. Each fluid channel of the plurality of fluid channels can comprise a terminus. In even further aspects, each fluidic chamber can comprise a fluid inlet in fluidic communication with the terminus of one of the plurality of fluid channels. Each fluidic chamber can also comprise an outlet vent at a fluidic pathway terminus. In some embodiments, the second piece of the assembly can comprise a transparent material that forms a first plurality of light pipes. In further embodiments, each light pipe of the first plurality of light pipes can be capable of transmitting light between one of the plurality of fluidic chambers and the single sensing region.

In an additional embodiment of the assembly, the assembly can further comprise a gasket located between the first piece and the second piece. In such embodiments, the gasket can be operatively coupled to the first piece and the second piece to form fluid seals in the continuous fluidic pathways. In a further embodiment, the gasket can comprise thermoplastic elastomeric (TPE) overmolding. The gasket can be pre-dried to a residual moisture of between 0-0.4% w/w. Alternatively, the gasket can be pre-dried to a residual moisture of at most 0.2% w/w. Based on this pre-drying of the gasket, the assembly can have a shelf stability that exceeds a threshold of 12 months. In some embodiments, a volume of the gasket can be compressed by 5%-25% when the first piece and the second piece of the assembly are operatively coupled.

In certain aspects, the biological assay is a diagnostic test. In some embodiments of the assembly, the first piece might further comprise a plurality of coupling handles and the second piece might further comprise a plurality of coupling latches. In a further embodiment, each of the plurality of coupling handles can be configured to operatively couple with one of the plurality of coupling latches.

In additional embodiments of the assembly, the outlet vent of each fluidic chamber can be sealed by a self-sealing vent material. The self-sealing vent material can be pre-dried to a residual moisture of between 0-0.4% w/w. Alternatively, the self-sealing vent material can be pre-dried to a residual moisture of at most 0.2% w/w. Based on this pre-drying of the self-sealing vent material, the assembly can have a shelf stability that exceeds a threshold of 12 months.

In some embodiments, the assembly further comprises a hydrophobic membrane that is located between the first piece and the second piece. In certain embodiments, the hydrophobic membrane is operatively coupled to the first piece and the second piece to form fluid seals in the continuous fluidic pathways. In further embodiments, the hydrophobic membrane can be welded to at least one of the first piece and the second piece using a plurality of energy directors. In even further embodiments, the outlet vent of each fluidic chamber is sealed by the hydrophobic membrane. The hydrophobic membrane can comprise polytetrafluoroethylene. The hydrophobic membrane can be pre-dried to a residual moisture of between 0-0.4% w/w. Alternatively, the hydrophobic membrane can be pre-dried to a residual moisture of at most 0.2% w/w. Based on this pre-drying of the hydrophobic membrane, the assembly can have a shelf stability that exceeds a threshold of 12 months.

In certain embodiments of the assembly, the first piece and/or the second piece can be injection molded. In some embodiments, the second piece comprises a material selected from the group consisting of polymethlamethacrylate, polystyrene, polycarbonate, polypropylene, polyethylene, polyethylene terephthalate, cyclic olefin copolymer, and polyamide, and combinations thereof. The first piece and the second piece can be pre-dried to a residual moisture of between 0-0.4% w/w in some embodiments. In alternative embodiments, the first piece and the second piece can be pre-dried to a residual moisture of at most 0.2% w/w. Based on this pre-drying of the first piece and the second piece, the assembly can have a shelf stability that exceeds a threshold of 12 months.

A volume of at least one of the plurality of fluidic chambers can differ from a volume of at least one other of the plurality of fluidic chambers in some embodiments of the assembly. In alternative embodiments, a volume of each of the plurality of fluidic chambers can be between 1 uL and 1100 uL. In further embodiments, the volume of each of the plurality of fluidic chambers is the same. In yet further embodiments the volume of each of the plurality of fluidic chambers is on the order of 30 uL.

In certain aspects of the assembly, at least one fluidic chamber of the plurality of fluidic chambers comprises dried reagents. In certain aspects the dried reagents are lyophilized reagents. The dried or lyophilized reagents can comprise reagents for carrying out an assay reaction on the samples. In some embodiments, the assay reagents comprise a nucleic acid amplification enzyme and a DNA primer.

The assembly can further comprise a circuit board operatively coupled to the fluidic chambers, in some embodiments. In further embodiments, the circuit board can further comprise a microprocessor. The circuit board can comprise a plurality of light emitting elements, each light emitting element capable of individually illuminating one of the plurality of fluidic chambers. In some embodiments, the plurality of light emitting elements can comprise LEDs. In alternative embodiments, the plurality of light emitting elements can comprise lasers. In some embodiments, the microprocessor is programmed to cause each of the plurality of light emitting elements to emit light in a repeating pattern having a repetition frequency ranging from 0.01-100 Hz, wherein only one of the plurality of fluidic chambers is illuminated at any time. In further embodiments, each of the plurality of the fluidic chambers is individually illuminated during each repetition of the pattern.

In some embodiments of the assembly, the circuit board comprises a photosensor optically coupled to the single sensing region. The photosensor can comprise one of a CMOS chip, a photodiode, a phototransistor, a photocell, and a photomultiplier tube. In some embodiments, the photosensor is configured to detect a color change. In further embodiments the photosensor is configured to detect an absorbance change. The microprocessor can be programmed to analyze signals received from the photosensor.

The circuit board of the assembly can further comprise a heating element comprising a ring shape in some embodiments. In further embodiments, the heating element can be configured to heat the plurality of fluidic chambers. The microprocessor can be programmed to generate signals transmitted to the heating element. The circuit board can also comprise a thermal pad comprising a ring shape, the thermal pad configured to transfer heat from the heating element to the plurality of fluidic chambers. Additionally, the circuit board can comprise a temperature sensor. The microprocessor can be programmed to analyze signals received from the temperature sensor.

The circuit board of the assembly can also comprise an electronic result display mechanism. The microprocessor can be programmed to generate signals transmitted to the electronic result display mechanism in some embodiments to simply and unambiguously indicate a result of an assay reaction carried out in one or more of the plurality of fluidic chambers.

In some aspects, each light pipe of the first plurality of light pipes comprises at least one of one or more reflecting surfaces and one or more refracting surfaces configured to direct light between one of the plurality of fluidic chambers and the single sensing region. In further embodiments, the second piece of the assembly further comprises a transparent material forming a second plurality of light pipes and each capable of transmitting light between one of the plurality of light emitting elements and one of the plurality of fluidic chambers. In even further embodiments, each light pipe of the second plurality of light pipes further comprises at least one of one or more reflecting surfaces and one or more refracting surfaces configured to direct light between one of the plurality of light emitting elements and one of the plurality of fluidic chambers.

In certain embodiments of the disclosed assembly, the plurality of fluid channels radially extend from the common sample receiving inlet. Furthermore, the plurality of fluidic chambers can be radially-arranged around the single sensing region. In certain aspects, the first plurality of light pipes are radially-arranged around the single sensing region. In additional aspects, the single sensing region is located at or near a center region of the second piece. In some aspects, the center region is defined with respect to the locations of the plurality of fluidic chambers. The first face and/or the second face can be radially-symmetric in some embodiments of the disclosed assembly.

In another aspect, the disclosure provides a system for performing a biological assay. In some embodiments, the system comprises an assembly and a circuit board. The assembly can comprise a first piece comprising a first face and a second piece comprising a second face. The first piece and the second piece can be operatively coupled to create a plurality of independent, continuous fluidic pathways. In certain embodiments, the continuous fluidic pathways comprise a common sample receiving inlet, a plurality of fluid channels, and a plurality of fluidic chambers. In some aspects, the plurality of fluid channels can extend from and can be in fluidic communication with the common sample receiving inlet. In further embodiments, each fluidic chamber of the plurality of fluidic chambers can be substantially equidistant from a single sensing region. As used herein, "substantially equidistant" means that a distance of each fluidic chamber of the plurality of fluidic chambers from the single sensing region, differs from a distance of each other fluidic chamber of the plurality of fluidic chambers from the single sensing region by no more than +/−25%. Each fluid channel of the plurality of fluid channels can comprise a terminus. In even further aspects, each fluidic chamber can comprise a fluid inlet in fluidic communication with the terminus of one of the plurality of fluid channels. Each fluidic chamber can also comprise an outlet vent at a fluidic pathway terminus. In some embodiments, the second piece of the assembly can comprise a transparent material that forms a first plurality of light pipes. In further embodiments, each light pipe of the first plurality of light pipes can be capable of transmitting light between one of the plurality of fluidic chambers and the single sensing region.

In some embodiments, the circuit board of the system is coupled to the fluidic chambers of the assembly and comprises a microprocessor, a plurality of light emitting elements, a photosensor, a heating element, a temperature sensor, and an electronic result display mechanism. In certain aspects, each light emitting element of the plurality of light emitting elements is capable of individually illuminating one of the plurality of fluidic chambers of the assembly. In further aspects, the photosensor is optically coupled to the single sensing region. The heating element can comprise a ring shape, and can be configured to heat the plurality of fluidic chambers of the assembly. In certain embodiments, the microprocessor is programmed to cause each of the plurality of light emitting elements to emit light in a repeating pattern at a repetition frequency, wherein only one of the plurality of fluidic chambers is illuminated at any time. In further embodiments, the microprocessor is further programmed to analyze signals received from the photosensor, to generate signals transmitted to the heating element, to analyze signals received from the temperature sensor, and to generate signals transmitted to the electronic result display mechanism. In some embodiments the signals transmitted to the electronic display mechanism cause the display to simply and unambiguously indicate a result of an assay reaction carried out in one or more of the plurality of fluidic chambers.

In an additional embodiment of the system, the system can further comprise a gasket located between the first piece and the second piece. In such embodiments, the gasket can be operatively coupled to the first piece and the second piece to form fluid seals in the continuous fluidic pathways. In a further embodiment, the gasket can comprise thermoplastic elastomeric (TPE) overmolding. The gasket can be pre-dried to a residual moisture of between 0-0.4% w/w. Alternatively, the gasket can be pre-dried to a residual moisture of at most 0.2% w/w. Based on this pre-drying of the gasket, the system can have a shelf stability that exceeds a threshold of 12 months. In some embodiments, a volume of the gasket can be compressed by 5%-25% when the first piece and the second piece of the system are operatively coupled.

In certain aspects, the biological assay is a diagnostic test. In some embodiments of the system, the first piece can further comprise a plurality of coupling handles and the second piece can further comprise a plurality of coupling latches. In a further embodiment, each of the plurality of coupling handles can be configured to operatively couple with one of the plurality of coupling latches.

In additional embodiments of the system, the outlet vent of each fluidic chamber can be sealed by a self-sealing vent material. The self-sealing vent material can be pre-dried to a residual moisture of between 0-0.4% w/w. Alternatively, the self-sealing vent material can be pre-dried to a residual moisture of at most 0.2% w/w. Based on this pre-drying of the self-sealing vent material, the system can have a shelf stability that exceeds a threshold of 12 months.

In some embodiments, the system further comprises a hydrophobic membrane that is located between the first piece and the second piece. In certain embodiments, the hydrophobic membrane is operatively coupled to the first piece and the second piece to form fluid seals in the continuous fluidic pathways. In further embodiments, the hydrophobic membrane can be welded to at least one of the first piece and the second piece using a plurality of energy directors. In even further embodiments, the outlet vent of each fluidic chamber is sealed by the hydrophobic membrane. The hydrophobic membrane can comprise polytetrafluoroethylene. The hydrophobic membrane can be pre-dried to a residual moisture of between 0-0.4% w/w. Alternatively, the hydrophobic membrane can be pre-dried to a residual moisture of at most 0.2% w/w. Based on this pre-drying of the hydrophobic membrane, the system can have a shelf stability that exceeds a threshold of 12 months.

In certain embodiments of the system, the first piece and/or the second piece can be injection molded. In some embodiments, the second piece comprises a material selected from the group consisting of polymethlamethacrylate, polystyrene, polycarbonate, polypropylene, polyethylene, polyethylene terephthalate, cyclic olefin copolymer, polyamide, and combinations thereof. The first piece and the second piece can be pre-dried to a residual moisture of between 0-0.4% w/w in some embodiments. In alternative embodiments, the first piece and the second piece can be pre-dried to a residual moisture of at most 0.2% w/w. Based on this pre-drying of the first piece and the second piece, the system can have a shelf stability that exceeds a threshold of 12 months.

A volume of at least one of the plurality of fluidic chambers can differ from a volume of at least one other of the plurality of fluidic chambers in some embodiments of the system. In alternative embodiments, a volume of each of the plurality of fluidic chambers can be between 1 uL and 1100 uL. In further embodiments, the volume of each of the plurality of fluidic chambers is on the order of 30 uL.

In certain aspects of the system, at least one fluidic chamber of the plurality of fluidic chambers comprises dried reagents. In some embodiments, the dried reagents are lyophilized reagents. The dried or lyophilized reagents can comprise reagents for carrying out an assay reaction on the sample. In some embodiments, the assay reagents comprise a nucleic acid amplification enzyme and a DNA primer.

In some embodiments, the plurality of light emitting elements can comprise LEDs. In alternative embodiments, the plurality of light emitting elements can comprise lasers. In some embodiments, the microprocessor is programmed to cause each of the plurality of light emitting elements to emit light in a repeating pattern having a repetition frequency ranging from 0.01-100 Hz. In further embodiments, each of the plurality of the fluidic chambers is individually illuminated during each repetition of the pattern.

In some embodiments of the system, the photosensor can comprise one of a CMOS chip, a photodiode, a phototransistor, a photocell, and a photomultiplier tube. In some embodiments, wherein photosensor is configured to detect a color change. In further embodiments the photosensor is configured to detect an absorbance change.

In some embodiments, the circuit board can also comprise a thermal pad comprising a ring shape, the thermal pad configured to transfer heat from the heating element to the plurality of fluidic chambers.

In some aspects, each light pipe of the first plurality of light pipes comprises at least one of one or more reflecting surfaces and one or more refracting surfaces configured to direct light between one of the plurality of fluidic chambers and single sensing region. In further embodiments, the second piece of the system further comprises a transparent material forming a second plurality of light pipes and each capable of transmitting light between one of the plurality of light emitting elements and one of the plurality of fluidic chambers. In even further embodiments, each light pipe of the second plurality of light pipes further comprises at least one of one or more reflecting surfaces and one or more refracting surfaces configured to direct light between one of the plurality of light emitting elements and one of the plurality of fluidic chambers.

In certain embodiments of the disclosed system, the plurality of fluid channels radially extend from the common sample receiving inlet. Furthermore, the plurality of fluidic chambers can be radially-arranged around the single sensing region. In certain aspects, the first plurality of light pipes are radially-arranged around the single sensing region. In additional aspects, the single sensing region is located at or near a center region of the second piece. In some aspects, the center region is defined with respect to the locations of the plurality of fluidic chambers. The first face and/or the second face can be radially-symmetric in some embodiments of the disclosed system.

In yet another aspect, the disclosure provides a method of determining one or more characteristics of a nucleic acid amplification sample based on a modified optical property of the sample. In some embodiments, the method comprises providing a biological sample comprising a nucleic acid, combining the biological sample with an optical property modifying reagent solution to produce a sample solution, inserting the sample solution into the common sample receiving inlet of the system described above, transmitting at least a portion of the sample solution into the fluid inlets of the plurality of fluidic chambers of the system described above, wherein the fluidic chambers comprise assay reagents, thereby generating a nucleic acid reaction mixture, heating the reaction mixture with the heating element of the system described above, the reaction generating an amplified nucleic acid and a plurality of protons, reacting the protons with the optical property modifying reagent, wherein the reacting is capable of modifying an optical property of the optical property modifying reagent to allow detection of the modified optical property indicative of the presence of a suspected analyte in the biological sample, causing each of the plurality of light emitting elements to emit light in the repeating pattern at the repetition frequency using the microprocessor of the system described above, determining one or more characteristics of the sample using the photosensor of the system described above based on the modified optical property, and simply and unambiguously indicating a result of the reaction carried out in one or more of the plurality of fluidic chambers using the electronic result display mechanism of the system described above. In some embodiments, transmitting at least the portion of the sample solution into the fluid inlets of the plurality of fluidic chambers further comprises transmitting at least the portion of the sample solution out of the common sample receiving inlet, into the plurality of extending fluid channels, out of the termini of the plurality of fluid channels, and into the fluid inlets of the plurality of fluidic chambers. In further embodiments, heating the reaction mixture promotes a nucleic acid amplification reaction using the nucleic acid present in the biological sample and the assay reagents, thereby generating an amplified nucleic acid and a plurality of protons.

In some embodiments of the method, each light emitting element individually illuminates one of the plurality of fluidic chambers. Furthermore, each of the plurality of the fluidic chambers can be individually illuminated during each repetition of the repeating pattern. In further aspects, causing each of the plurality of light emitting elements to emit light in the repeating pattern further comprises causing each of the plurality of light emitting elements to emit light at a different and distinct time such that only one of the plurality of fluidic chambers is illuminated at any time. In some embodiments, the repetition frequency ranges from 0.01-100 Hz.

In certain embodiments of the method, the light emitted by each of the plurality of light emitting elements is transmitted to the plurality of fluidic chambers through the second plurality of light pipes of the system described above. In even further aspects, the light emitted by each of the plurality of light emitting elements is transmitted to the plurality of fluidic chambers through the second plurality of light pipes using at least one of one or more reflecting surfaces and one or more refracting surfaces located within the second plurality of light pipes. Additionally, the light emitted by each of the plurality of light emitting elements can be transmitted to the photosensor through the first plurality of light pipes of the second piece of the system described above. Furthermore, the light emitted by each of the plurality of light emitting elements can be transmitted to the photosensor through the first plurality of light pipes using at least one of one or more reflecting surfaces and one or more refracting surfaces located within the first plurality of light pipes.

In some aspects, heating the reaction mixture with the heating element further comprises transmitting signals generated by the microprocessor to the heating element. Furthermore, determining one or more characteristics of the sample using the photosensor can further comprise the microprocessor analyzing signals received from the photosensor. Additionally, the method can further comprise receiving signals from the temperature sensor of the system described above and analyzing the signals received from the temperature sensor using the microprocessor. In additional aspects of the method, displaying the determined characteristics using the electronic result display mechanism further comprises transmitting signals generated by the microprocessor to the electronic result display mechanism to simply and unambiguously indicate a result of the reaction carried out in one or more of the plurality of fluidic chambers.

In certain embodiments, determining one or more characteristics of the sample using the photosensor further comprises detecting a color change of the sample using the photosensor. In further embodiments, determining one or more characteristics of the sample using the photosensor further comprises detecting an absorbance change of the sample using the photosensor.

In some embodiments, the method further comprises pre-drying the self-sealing vent material, the first and the second piece, the hydrophobic membrane, and/or the gasket of the system described above to a residual moisture of between 0-0.4% w/w. Alternatively, the method can further comprise pre-drying the self-sealing vent material, the first and the second piece, the hydrophobic membrane, and/or the gasket of the system described above to a residual moisture of at most 0.2% w/w.

In some embodiments of the method, the optical property modifying reagent solution comprises a liquid buffer. Additionally, the assay reagents can comprise nucleic acid amplification enzymes and DNA primers. In further embodiments of the method, the assay reagents are dried, and can comprise lyophilized reagents.

BRIEF DESCRIPTION OF THE DRAWINGS

The present application is further understood when read in conjunction with the appended drawings. For the purpose of illustrating the subject matter, there are shown in the drawings exemplary embodiments of the subject matter; however, the presently disclosed subject matter is not limited to the specific methods, devices, and systems disclosed. In addition, the drawings are not necessarily drawn to scale. In the drawings:

FIG. 2A is an illustration of a radially-symmetric circular second face of the second piece with radially-arranged fluidic chambers and first light pipes, in accordance with an embodiment.

FIG. 2B is an illustration of a radially-symmetric polygon second face of the second piece with radially-arranged fluidic chambers and first light pipes, in accordance with an embodiment.

FIG. 2C is an illustration of a non-radially-symmetric semi-circular second face of the second piece with radially-arranged fluidic chambers and first light pipes, in accordance with an embodiment.

FIG. 2D is an illustration of a non-radially-symmetric circular second face of the second piece with radially-arranged fluidic chambers and first light pipes, in accordance with an embodiment.

FIG. 2E is an illustration of a non-radially-symmetric circular second face of the second piece with radially-arranged fluidic chambers and first light pipes, in accordance with an embodiment.

FIG. 2F is an illustration of a radially-symmetric square second face of the second piece with radially-arranged fluidic chambers and first light pipes, in accordance with an embodiment.

FIG. 3A is an illustration of an aerial view of uncoupled components of the device for performing biological assays, in accordance with an embodiment.

FIG. 3B is an illustration of an underside view of the uncoupled components of the device for performing biological assays, in accordance with an embodiment.

FIG. 3C is an illustration of an aerial view of alternative uncoupled components of the device for performing biological assays, in accordance with an embodiment.

FIG. 3D is an illustration of an underside view of the alternative uncoupled components of the device for performing biological assays, in accordance with an embodiment.

DETAILED DESCRIPTION

Figure 1:
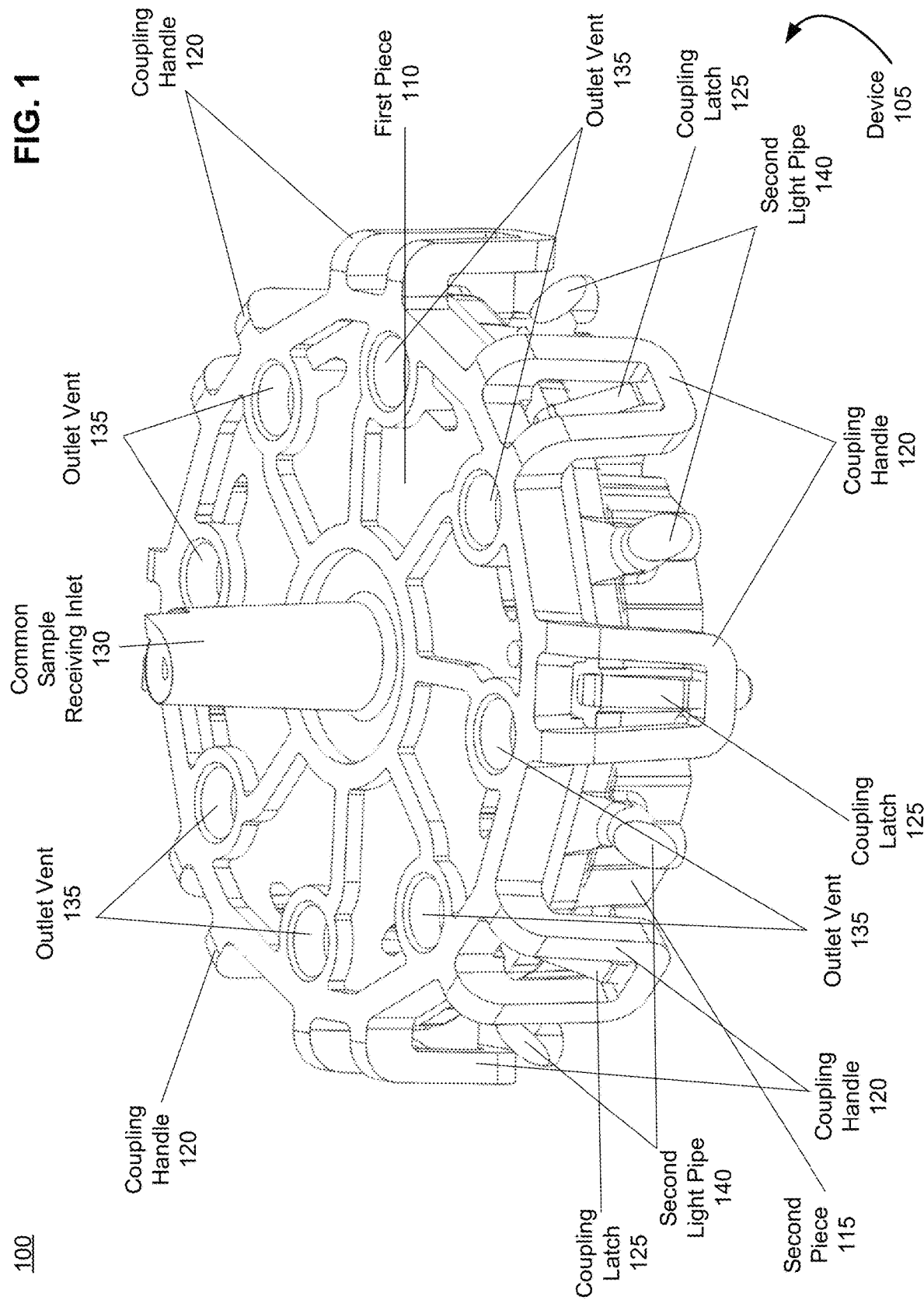
FIG. 1 is an illustration of a device for performing biological assays, in accordance with an embodiment.

Devices, systems, and methods for performing biological assays using indicators that modify one or more optical properties of the assayed biological samples or aspects thereof are provided. The subject methods include generating a reaction product by carrying out a biochemical reaction on the sample introduced to a device and reacting the reaction product with an indicator capable of generating a detectable change in an optical property of the sample to indicate the presence, absence, or amount of analyte suspected to be present in the sample.

Before the present invention is described in greater detail, it is to be understood that this invention is not limited to particular embodiments described, as such can, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges can independently be included in the smaller ranges and are also encompassed within the invention, subject to any specifically excluded limit in the stated range. Where the stated range includes one or both of the limits, ranges excluding either or both of those included limits are also included in the invention.

Certain ranges can be presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number can be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided can be different from the actual publication dates which can need to be independently confirmed.

It is noted that, as used herein and in the appended claims, the singular forms "a," "an," and "the" include plural referents unless the context clearly dictates otherwise. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation.

Additionally, certain embodiments of the disclosed devices and/or associated methods can be represented by drawings which can be included in this application. Embodiments of the devices and their specific spatial characteristics and/or abilities include those shown or substantially shown in the drawings or which are reasonably inferable from the drawings. Such characteristics include, for example, one or more (e.g., one, two, three, four, five, six, seven, eight, nine, or ten, etc.) of: symmetries about a plane (e.g., a cross-sectional plane) or axis (e.g., an axis of symmetry), edges, peripheries, surfaces, specific orientations (e.g., proximal; distal), and/or numbers (e.g., three surfaces; four surfaces), or any combinations thereof. Such spatial characteristics also include, for example, the lack (e.g., specific absence of) one or more (e.g., one, two, three, four, five, six, seven, eight, nine, or ten, etc.) of: symmetries about a plane (e.g., a cross-sectional plane) or axis (e.g., an axis of symmetry), edges, peripheries, surfaces, specific orientations (e.g., proximal), and/or numbers (e.g., three surfaces), or any combinations thereof.

As will be apparent to those of skill in the art upon reading this disclosure, each of the individual embodiments described and illustrated herein has discrete components and features which can be readily separated from or combined with the features of any of the other several embodiments without departing from the scope or spirit of the present invention. Any recited method can be carried out in the order of events recited or in any other order which is logically possible.

In further describing the subject invention, subject devices for use in practicing the subject devices will be discussed in greater detail, followed by a review of associated methods.

Definitions

Terms used in the claims and specification are defined as set forth below unless otherwise specified.

The term "colorimetry" or "colorimetric" refers to techniques of quantifying or otherwise observing colored compound concentrations in solution. "Colorimetric detection" refers to any method of detecting such colored compounds and/or the change in color of the compounds in solution. Methods can include visual observation, absorbance measurements, or fluorescence measurements, among others.

The term "halochromic agent" refers to a composition that changes color upon some chemical reaction. In particular, a halochromic agent can refer to a composition that changes color with a pH change. Different halochromic agents can change colors over different pH transition ranges.

The term "transition pH range" or "pH transition range" refers to a pH range over which the color of a particular sample or compound changes. A specific transition pH range for a sample can depend on a halochromic agent in the sample (see above).

The term "nucleic acid amplification" or "amplification reaction" refers to methods of amplifying DNA, RNA, or modified versions thereof. Nucleic acid amplification includes several techniques, such as an isothermal reaction or a thermocycled reaction. More specifically, nucleic acid amplification includes methods such as polymerase chain reaction (PCR), loop-mediated isothermal amplification (LAMP), strand displacement amplification (SDA), recombinase polymerase amplification (RPA), helicase dependent amplification (HDA), multiple displacement amplification (MDA), rolling circle amplification (RCA), and nucleic acid sequence-based amplification (NASBA). The term "isothermal amplification" refers to an amplification method that is performed without changing the temperature of the amplification reaction. Protons are released during an amplification reaction: for every deoxynucleotide triphosphate (dNTP) that is added to a single-stranded DNA template during an amplification reaction, one proton (Hf) is released.

The term "sufficient amount" means an amount sufficient to produce a desired effect, e.g., an amount sufficient to modulate protein aggregation in a cell.

Devices

Aspects of the subject disclosure include devices for performing biological assays by modifying optical properties of biological samples and detecting these modified properties. As used herein, a "biological sample" is a sample containing a quantity of organic material, e.g., one or more organic molecules, such as one or more nucleic acids e.g., DNA and/or RNA or portions thereof, which can be taken from a subject. As such, a "biological sample assay" is test on a biological sample which is performed to evaluate one or more characteristics of the sample. In some aspects a biological sample is a nucleic acid amplification sample, which is a sample including or suspected of including one or more nucleic acids or portions thereof which can be amplified according to the subject embodiments.

A biological sample can be provided by a subject and include one or more cells, such as tissue cells of the subject. As used herein, the term "tissue" refers to one or more aggregates of cells in a subject (e.g., a living organism, such as a mammal, such as a human) that have a similar function and structure or to a plurality of different types of such aggregates. Tissue can include, for example, organ tissue, muscle tissue (e.g., cardiac muscle; smooth muscle; and/or skeletal muscle), connective tissue, nervous tissue and/or epithelial tissue. Tissue can, in some versions, include cells from the inside of a subject's cheek and/or cells in a subject's saliva.

As noted above, a biological sample can be provided by a subject. In certain embodiments, a subject is a "mammal" or a "mammalian" subject, where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In some embodiments, the subject is a human. The term "humans" can include human subjects of both genders and at any stage of development (e.g., fetal, neonates, infant, juvenile, adolescent, and adult), where in certain embodiments the human subject is a juvenile, adolescent or adult. While the devices and methods described herein can be applied in association with a human subject, it is to be understood that the subject devices and methods can also be applied in association with other subjects, that is, on "non-human subjects."

A biological sample, as referred to herein, can in some versions be a prepared biological sample. A prepared biological assay sample is a biological assay sample which has been processed for example by exposing the sample to a preparation solution, such as a solution including a lysing agent, such as a detergent. Accordingly, in some embodiments, a biological sample is a lysate. Such preparation can enable the prepared biological sample to react, for example, with assay reagents and/or an optical property modifying reagent upon exposure thereto. The exposure can include lysing cells of the sample with a lysing agent of the preparation solution and/or extracting nucleic acids therefrom. Such extracted nucleic acids can be released into a resulting prepared sample solution. In some embodiments, a step of extracting genomic deoxyribonucleic acid (DNA) from a biological sample is included. Where desired, the preparation solution is a nucleic acid amplification preparation solution and exposure to the solution prepares nucleic acids of the sample for amplification, e.g., isothermal amplification.

Also, as used herein, the phrase "optical property," refers to one or more optically-recognizable characteristics, such as a characteristic resulting from wavelength and/or frequency of radiation, e.g., light, emitted by or transmitted through a sample, prior to, during, or following an assay reaction carried on using said sample, such as color, absorbance, reflectance, scattering, fluorescence, phosphorescence, etc. As such, modifying an optical property refers to changing such a characteristic.

FIG. 1 is an illustration 100 of a device 105 for performing biological assays, in accordance with an embodiment. In various embodiments, the device 105 comprises a first piece 110 and a second piece 115. In some embodiments, at least one of the first piece 110 and the second piece 115 are injection molded. In alternative embodiments, one of the first piece 110 and the second piece 115 can not be injection molded. For example, one of the first piece 110 and the second piece 115 can comprise a membrane.

In various embodiments, the device 105, including the first piece 110 and the second piece 115, comprises one or more materials including, for example, polymeric materials (e.g., materials having one or more polymers including, for example, plastic and/or rubber) and/or metallic materials. Materials of which any of the device 105 can be composed include, but are not limited to: polymeric materials, e.g., elastomeric rubbers, such as natural rubber, silicone rubber, ethylene-vinyl rubber, nitrile rubber, butyl rubber; plastics, such as polytetrafluoroethene or polytetrafluoroethylene (PFTE), including expanded polytetrafluoroethylene (e-PFTE), polyethylene, polyester (Dacron™), nylon, polypropylene, polyethylene, high-density polyethylene (HDPE), polyurethane, polydimethyisiloxane (PDMS); or adhesives, such as, acrylic adhesive, silicone adhesive, epoxy adhesive, or any combination thereof, etc., metals and metal alloys, e.g., titanium, chromium, aluminum, stainless steel, etc., and the like. In various embodiments, the materials are transparent materials and as such, allow light within the visible spectrum to efficiently pass therethrough.

In some embodiments, the first piece 110 and the second piece 115 can be pre-dried to a residual moisture of between 0-0.4% w/w. In a preferred embodiment, the first piece 110 and the second piece 115 can be pre-dried to a residual moisture of at most 0.2% w/w. Based on this pre-drying of the first piece 110 and the second piece 115, the device 105 can have a shelf stability that exceeds a threshold of 12 months.

The first piece 110 comprises a first face and the second piece 115 comprises a second face. The faces of the first piece 110 and the second piece 115 can comprise any shape. Furthermore, the faces of the first piece 110 and the second piece 115 can be radially-symmetric or non-radially-symmetric. However in a preferred embodiment, the first face and the second face are radially-symmetric and/or substantially radially-symmetric. For example, the faces of the first piece 110 and the second piece 115 can comprise a circle, a hexagon, and/or another multi-sided polygon. Multiple embodiments of both radially-symmetric and non-radially-symmetric faces of the second piece 115 are shown in FIGS. 2A-F and are discussed with regard to FIGS. 2A-F below. The advantages of the first piece 110 and the second piece 115 being at least substantially radially-symmetric are discussed in greater detail below with regard to FIGS. 2A-F and 4.

As noted above and shown in FIG. 1, the first piece 110 can be coupled to the second piece 115 to form the unitary device 105. In some embodiments, the first piece 110 is operatively coupled to the second piece 115. "Operatively coupled," "operatively connected," and "operatively attached" as used herein means connected in a specific way that allows the disclosed devices to operate and/or methods to be carried out effectively in the manner described herein. For example, operatively coupling can include removably coupling or fixedly coupling two or more aspects. Operatively coupling can also include fluidically and/or electrically and/or mateably and/or adhesively coupling two or more components. Also, by "removably coupled," as used herein, is meant coupled, e.g., physically and/or fluidically and/or electrically coupled, in a manner wherein the two or more coupled components can be un-coupled and then re-coupled repeatedly. For example, in some embodiments, the first piece 110 is operatively coupled to the second piece 115 to create a plurality of independent, continuous fluidic pathways.

In some embodiments, the first piece 110 and the second piece 115 are coupled using a plurality of coupling handles 120 and a plurality of coupling latches 125. As shown in FIG. 1, the plurality of coupling handles 120 are attached to the first piece 110 and the plurality of coupling latches 125 are attached to the second piece 115. The plurality of coupling handles 120 are configured to operatively couple with the plurality of coupling latches 125. Additional methods for coupling of the first piece 110 and the second piece 115 are discussed in greater detail below with regard to FIGS. 3A and 3B.

As noted above, in certain embodiments, operably coupling the first piece 110 and the second piece 115 creates a plurality of independent, continuous fluidic pathways. The plurality of independent, continuous fluidic pathways comprise a common sample receiving inlet 130, a plurality of fluid channels (shown in FIG. 3B), and a plurality of fluidic chambers (shown in FIG. 2). Specifically, each fluidic pathway comprises the common sample receiving inlet 130, one fluid channel of the plurality of fluid channels, and one fluidic chamber of the plurality of fluidic chambers. As discussed above, this creation of the plurality of independent, continuous fluidic pathways is advantageous because it enables multiple assays to occur in parallel.

In some embodiments, the common sample receiving inlet 130 is located in a center of the operatively coupled first piece 110 and second piece 115. In some aspects, the center region is defined with respect to the locations of the plurality of fluidic chambers. In alternative embodiments, the common sample receiving inlet 130 can not be off-centered with respect to the operatively coupled first piece 110 and second piece 115. The common sample receiving inlet 130 is configured to receive a sample solution. In some embodiments, the sample solution includes a biological sample. This biological sample can include nucleic acids. In some embodiments, the sample solution also includes additional reagents. For example, the sample solution can include an optical property modifying reagent solution. This optical property modifying reagent solution can further comprise an optical property modifying reagent as well as a liquid buffer. According to some embodiments, an optical property of an optical property modifying reagent is changed due to the presence or the absence of a particular marker in a biological sample when the biological sample or one or more aspect thereof, are exposed to the optical property modifying reagent. Examples of optical properties that can change include color and absorbance. Changes in optical properties can be detected and used to identify properties of the biological sample. Optical property modifying reagents and detection of changes in their optical properties are discussed in greater detail with regard to FIGS. 4, 5, and 11.

The plurality of fluid channels extend from and are in fluidic communication with the common sample receiving inlet 130 such that fluid can travel from the common sample receiving inlet 130 into the plurality of fluid channels. For example, in embodiments such as those discussed above, the biological sample can travel from the common sample receiving inlet 130 into the plurality of fluid channels. In some embodiments, the fluid channels radially extend from the common sample receiving inlet 130.

Each of the fluid channels can be shaped as a cylinder or a quadrilateral prism and can have dimensions including a length of 10 m or less, such as 1 m or less, such as 10 cm or less, such as 1 mm or less, and/or have a diameter, width and/or height of 100 mm or less, such as 10 mm or less, such as 1 mm or less, such as 0.1 mm or less, such as 10 micrometers or less. Each of the fluid channels can also have a volume of 1100 µL or less, such as 10 µL or less, such as 1 µL or less, such as 0.1 µL or less, such as 1 nL or less. In a preferred embodiment, the dimensions of each fluid channel of the plurality of fluid channels are the same.

The fluid channels extend from the common sample receiving inlet 130 to the plurality of fluidic chambers. Specifically, each fluidic channel extends from the common sample receiving inlet 130 to one of the plurality of fluidic chambers. Furthermore, each fluid channel ends in a terminus (shown in FIG. 3B) and each fluidic chamber comprises a fluid inlet (shown in FIG. 3B). Thus the terminus of each fluidic channel is in fluidic communication with the fluid inlet of the one fluidic chamber to which the fluidic channel extends. In other words, fluid is able to flow from the terminus of the fluid channel into the fluid inlet of the fluidic chamber. After fluid passes through the fluid inlet, the fluid is located within the fluidic chamber.

Figure 4:
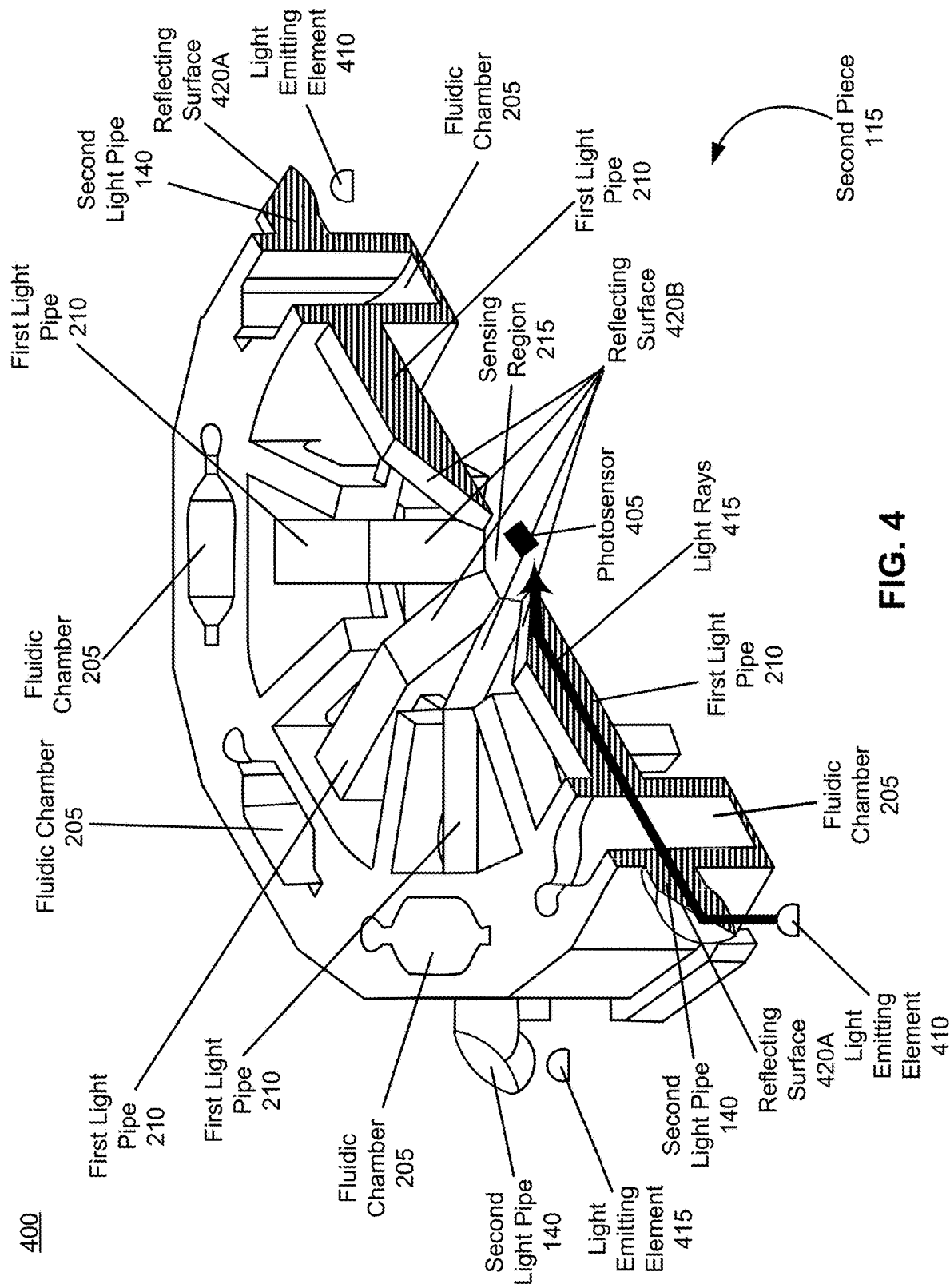
FIG. 4 is an illustration of a cross-section of the second piece of the device for performing biological assays, in accordance with an embodiment.

In some embodiments, each fluidic chamber of the plurality of fluidic chambers is substantially equidistant from a single sensing region (shown in FIG. 4). In further embodiments, each fluidic chamber of the plurality of fluidic chambers is substantially equidistant from the common sample receiving inlet 130. As used herein, "substantially equidistant" means that a distance of each fluidic chamber of the plurality of fluidic chambers from the single sensing region, differs from a distance of each other fluidic chamber of the plurality of fluidic chambers from the single sensing region by no more than +/−25%. In even further embodiments, the dimensions of each fluid channel of the plurality of fluid channels comprise the same dimensions. In such embodiments, the distances traveled by fluid from the common sample receiving inlet 130 to each fluidic chamber are approximately equal and the times to travel from the common sample receiving inlet 130 to each fluidic chamber are also approximately equal. By approximately equal we contemplate differences less than or equal to about plus or minus 10% or less than or equal to plus or minus 5% of less than or equal to plus or minus 1% and intermediate ranges within these bounds. Such substantial equidistance between the fluidic chambers and the single sensing region, and substantial equidistance between the fluidic chambers and the common sample receiving inlet, as well as the similar dimensions of the fluid channels, furthers the ability of the device 105 to perform multiple assays in parallel under similar conditions. These similar conditions produce more controlled and reliable assay results.

Movement, e.g., diffusion, of a liquid or a component thereof from one fluidic chamber to another is substantially prevented by the fluid channels due to the length of the fluid channels. Accordingly, the fluidic chambers are isolated from one another and the amount of such movement over the duration of an assay is negligible in influencing an assay result.

Each fluidic chamber can be shaped as a cylinder, rectangular box, cube, or any combination thereof. Each fluidic chamber can also be a microfluidic chamber. For example, in certain embodiments, each fluidic chamber can have a volume of between 1 µL to 1100 µL. In a further embodiment, each fluidic chamber can have a volume of on the order of 30 µL. In an alternative embodiment, a volume of at least one of the plurality of fluidic chambers differs from a volume of at least one other of the plurality of fluidic chambers.

In some embodiments, each fluidic chamber comprises dried reagents, which can be lyophilized reagents. In some embodiments, the dried or lyophilized reagents comprise assay reagentss. In further embodiments, the assay reagents comprise a nucleic acid amplification enzyme and a DNA primer. In such embodiments, the assay reagents enable amplification of select nucleic acids present or suspected to be present in the biological sample. The assay reagents can be dried, e.g., lyophilized to prolong shelf stability of the assay reagents and thus of the device 105. The dried or lyophilized assay reagents located within the fluidic chambers are discussed in greater detail with regard to FIGS. 3A-E and 11.

In addition to comprising dried or lyophilized assay reagents, each fluidic chamber also comprises an outlet vent 135. The outlet vent 135 of each fluidic chamber designates the terminus of the independent, continuous fluidic pathway described above. In some embodiments, the outlet vents 145 can be sealed with a vent material (not shown).

The vent material sealing the outlet vents 145 can be porous and as such, have a plurality of pores extending therethrough. The vent material can also have a passively tunable porosity. The phrase "passively tunable porosity," as used herein, refers to the ability of having a first conformation in which one or more gasses, e.g., air, can pass therethrough, e.g., through pores, and a second conformation in which fluids including the one or more gasses and liquids, such as liquids including a biological sample, are prevented from passing therethrough, e.g., through the pores, and proceeding automatically from the first to the second conformation upon contact with a liquid. In the second conformation, the vent material prevents evaporation of the liquids therethrough, e.g., through the pores. Also, in the second conformation, the vent material can fluidically seal a fluidic chamber by covering its outlet vent 135 and preventing passage of fluid, including evaporation, therethrough. The vent material can be configured to proceed from the first conformation to the second conformation passively, e.g., automatically without user interaction, upon contacting the one or more liquids, such as liquids including a biological sample, with the vent material or a portion thereof, e.g., a surface, such as a surface forming a wall of a fluidic chamber. As such, in some versions, the vent material can be self-sealing to liquids and gasses when contacted by a liquid.

Also, one or more portions or materials of the vent material can have a passively tunable porosity. For example, in some versions, the vent material can be composed of a hydrogel having a passively tunable porosity. Such a hydrogel can be capable of swelling and reducing the porosity of the porous polymer matrix upon contact with a liquid, e.g., an aqueous liquid.

In alternative embodiments, the vent material can comprise a hydrophobic vent material. For example, the vent material can comprise polytetrafluoroethylene. Such embodiments are discussed in greater detail with regard to FIGS. 3C-E.

In further embodiments, the vent material can be composed of a variety of materials including one or more polymer matrix, such as a porous polymer matrix, such as polyethylene. The vent material can also be composed of a hydrogel such as carboxymethyl cellulose. Other materials of which the vent material or portions thereof, such as coatings, can also be composed include saccharides, proteins, deliquescent materials, nylon, ABS, polycarbonate, and Poly(methyl methacrylate), and other hygroscopinc materials, or any combinations thereof. The vent material can also be or include one or more coatings.

In certain embodiments, the vent material, such as the self-sealing vent material, can be pre-dried to a residual moisture before placement over the outlet vents 145. For example, in some embodiments, the vent material can be pre-dried to a residual moisture of between 0-0.4% w/w. In a preferred embodiment, the vent material can be pre-dried to a residual moisture of at most 0.2% w/w. By pre-drying the vent material, the shelf life of the vent material and thus the shelf stability of the device 105 can be extended. Specifically, by pre-drying the vent material the device 105 can achieve a shelf stability that exceeds a threshold of 12 months.

The final feature of the device 105 visible in FIG. 1 is a plurality of second light pipes 140. The plurality of second light pipes 140 are used in detection of optical properties of the biological sample. The plurality of second light pipes 140 are discussed in greater detail with regard to FIGS. 4 and 5.

FIGS. 2A-F are illustrations of various embodiments of second faces of the second piece 115. As discussed above with regard to FIG. 1, second faces of the second piece 115 can be radially-symmetric and/or non-radially-symmetric. In a preferred embodiment, second faces of the second piece 115 are radially-symmetric. Radial-symmetry of the second piece 115 (as well as the first piece 110 and the device 105 as a whole) is a preferred method of designing the device 105 so that each fluidic chamber of the plurality of fluidic chambers 205 is substantially equidistant from the sensing region 215, and more specifically, so that the light path lengths between each fluidic chamber 205 and the single sensing region 215 are substantially equal, as this substantial equidistance allows for more controlled and reliable assays. However, in alternative embodiments, a device 105 can not be radially-symmetric but can still maintain substantial equidistance between each fluidic chamber 205 and the sensing region 215. As used herein, "substantially equidistant" means that a distance of each fluidic chamber of the plurality of fluidic chambers from the single sensing region, differs from a distance of each other fluidic chamber of the plurality of fluidic chambers from the single sensing region by no more than +/−25%. In even further embodiments, a device 105 can be characterized by non-equivalent distances between one or more of the plurality of the fluidic chambers 205 and the sensing region 215.

Additionally, despite the fact that the fluidic chambers 205 and first light pipes 210 depicted in FIGS. 2A-F are radially-arranged around a single sensing region 215, in alternative embodiments, the fluidic chambers 205 and the first light pipes 210 can be non-radially-arranged around the single sensing region 215. Alternative arrangements of second faces of the second piece 115 not explicitly disclosed in FIGS. 2A-F are also possible.

FIG. 2A is an illustration 200A of a radially-symmetric circular second face of the second piece 115 with radially-arranged fluidic chambers 205 and first light pipes 210, in accordance with an embodiment. Specifically, the fluidic chambers 205 and the first light pipes 210 are radially-arranged around a single sensing region 215. Additionally, the fluidic chambers 205 and the first light pipes 210 are radially-symmetric. Note that the first light pipes 210 (discussed in greater detail with regard to FIGS. 4-6 below) are the paths through which light travels between the fluidic chambers 205 and the single sensing region 215. Thus radial-symmetry of the fluidic chambers 205 and the first light pipes 210 ensures that the light path lengths between each of the fluidic chambers 205 and the sensing region 215 are equal.

FIG. 2B is an illustration 200B of a radially-symmetric polygon second face of the second piece 115 with radially-arranged fluidic chambers 205 and first light pipes 210, in accordance with an embodiment. Specifically, the second polygon face is an octagon. The fluidic chambers 205 and the first light pipes 210 are radially-arranged around the single sensing region 215. Additionally, the fluidic chambers 205 are the first light pipes 210 are radially-symmetric.

FIG. 2C is an illustration 200C of a non-radially-symmetric semi-circular second face of the second piece 115 with radially-arranged fluidic chambers 205 and first light pipes 210, in accordance with an embodiment. Specifically, the semi-circular second face is a deformed semi-circle. The fluidic chambers 205 and the first light pipes 210 are radially-arranged around the single sensing region 215. However, because the semi-circular second face is not radial itself, the fluidic chambers 205 and the first light pipes 210 cannot be radially-symmetric around the second face.

FIG. 2D is an illustration 200D of a non-radially-symmetric circular second face of the second piece 115 with radially-arranged fluidic chambers 205 and first light pipes 210, in accordance with an embodiment. Specifically, the fluidic chambers 205 and the first light pipes 210 are radially-arranged around the single sensing region 205. Furthermore, the fluidic chambers 205 are each substantially equidistant from the single sensing region 215. As used herein, "substantially equidistant" means that a distance of each fluidic chamber of the plurality of fluidic chambers from the single sensing region, differs from a distance of each other fluidic chamber of the plurality of fluidic chambers from the single sensing region by no more than +/−25%. However, the circular second face is not radially-symmetric because the fluidic chambers 205 and the second light pipes 210 do not occur at even intervals along the radius of the circle.

FIG. 2E is an illustration 200E of a non-radially-symmetric circular second face of the second piece 115 with radially-arranged fluidic chambers 205 and first light pipes 210, in accordance with an embodiment. Specifically, the fluidic chambers 205 and the first light pipes 210 are radially-arranged around the single sensing region 205. However, the fluidic chambers 205 are not substantially equidistant from the single sensing region 215. Furthermore, the circular second face is not radially-symmetric because the fluidic chambers 205 do not have the same dimensions. As a result, the optical path lengths of the fluidic chambers 205 are not the equal.

FIG. 2F is an illustration 200F of a radially-symmetric square second face of the second piece 115 with radially-arranged fluidic chambers 205 and first light pipes, in accordance with an embodiment. The fluidic chambers 205 and the first light pipes 210 are radially-arranged around the single sensing region 215. Additionally, the fluidic chambers 205 are the first light pipes 210 are radially-symmetric.

FIG. 3A is an illustration of an aerial view 300A of uncoupled components of the device 105 for performing biological assays, in accordance with an embodiment. The uncoupled components of the device 105 include the first piece 110 and the second piece 115.

As discussed above with regard to FIG. 1, the first piece 110 and the second piece 115 can be operatively coupled to one another to create a plurality of independent, continuous fluidic pathways. In certain embodiments, the first piece 110 and the second piece 115 are operatively coupled with no components placed between the first piece 110 and the second piece 115. However in alternative embodiments such as the embodiment depicted in FIG. 3A, to operatively couple the first piece 110 and the second piece 115, a gasket 320 can be placed between the first piece 110 and the second piece 115. The gasket 320 can facilitate the formation of the plurality of independent, continuous fluidic pathways. In embodiments in which the gasket 320 is placed between the first piece 110 and the second piece 115 and the first piece 110 and the second piece 115 are operatively coupled, a volume of the gasket can be compressed by 5%-25%. In certain embodiments, the gasket 320 comprises thermoplastic elastomeric (TPE) overmolding. In such embodiments, the gasket 320 can be overmolded on the first piece 110 and/or the second piece 115 to promote sealing of the continuous fluidic pathways. In some embodiments, the gasket 320 can be pre-dried to a residual moisture of between 0-0.4% w/w. In a preferred embodiment, the gasket 320 can be pre-dried to a residual moisture of at most 0.2% w/w. Based on this pre-drying of the gasket 320, the device 105 can have a shelf stability that exceeds a threshold of 12 months.

In further embodiments (not shown), to operatively couple the first piece 110 and the second piece 115, an adhesive can be placed between the first piece 110 and the second piece 115. In even further embodiments (not shown), the device 105 can comprise a single, monolithic piece rather than two separate and operatively coupled pieces such as the first piece 110 and the second piece 115.

In some embodiments, the gasket 320 forms a wall of each of the plurality of fluidic chambers 205. In forming a wall, the gasket 320 can seal and/or extend over an opening at an end of the fluidic chamber 205. As such, the gasket 320 and/or a portion thereof, can define an end of the fluidic chamber 205 and/or sealably contain one or more solid and/or fluid media, e.g., a biological sample and/or an optical property modifying reagent and/or assay reagents, within the fluidic chamber 205.

The gasket 320 according to the subject embodiments can be or include a sheet, e.g., a solid sheet, of one or more materials, e.g., two materials, having a thin and/or planar shape. The gasket 320 can include a top surface and a bottom surface each defining a plane parallel with the other and separated by a thickness. In various embodiments, a sheet is or includes a uniform layer of a single material. The gasket 320 can also be composed of two or more, e.g., three, four, five, or more, etc. sheets laminated to one another. In some versions, the sheets are acrylic adhesive laminates.

The gasket 320 can, in some aspects, have a length, a width and a height, also referred to as a thickness. A thickness of the gasket 320, e.g., a thickness between a first surface and a second surface opposite the first surface, can be 5 mm or less, 3 mm or less, 1 mm or less, 0.5 mm or less, 0.1 mm or less, or 50 microns or less. A thickness of the gasket 320 and/or a sheet thereof can also range for example, from 5 mm to 50 microns, such as 3 mm to 0.1 mm, such as 1 mm to 0.1 mm, inclusive. Also, a length and/or width of the gasket 320 and/or a sheet can also range from 1 mm to 2 m, such as from 1 cm to 1 m, such as from 1 cm to 10 cm, such as from 1 cm to 5 cm.

The gasket 320 can be and/or have an area defining any suitable size or shape including a: circle, semi-circle, oval, rectangle, square, triangle, polygon, quadrilateral, or combination thereof. The gasket 320 can include one or more sheets of solid, uniform, integrated material, and in some versions, does not include any openings therethrough.

The gasket 320 and/or a sheet thereof can have three edges, four edges, or more than four edges which define the area of the gasket 320. In various embodiments, the edges meet at corners, e.g., three, four, five, or ten or more corners. In some versions, a first edge of the gasket 320 is opposite a second edge of the gasket 320 and adjacent to a third and/or fourth edge of the gasket 320. In such an embodiment, the third edge can be opposite a fourth edge and the fourth edge can be adjacent to the first and/or second edge.

According to the subject embodiments, the gasket 320 can be composed of a variety of materials. Sheets comprising the gasket 320 can be composed of the same or different materials. Such materials can have characteristics of flexibility and/or high strength (e.g., resistant to wear) and/or high fatigue resistance (e.g., able to retain its physical properties for long periods of time regardless of the amount of use or environment). Materials of interest of which the gasket 320 or portions thereof can be composed include, but are not limited to: polymeric materials, e.g., elastomeric rubbers, such as natural rubber, silicone rubber, ethylene-vinyl rubber, nitrile rubber, butyl rubber; plastics, such as polytetrafluoroethene or polytetrafluoroethylene (PFTE), including expanded polytetrafluoroethylene (e-PFTE), polyester (Dacron™), nylon, polypropylene, polyethylene, high-density polyethylene (HDPE), polyurethane; or adhesives, such as, acrylic adhesive, silicone adhesive, epoxy adhesive, or any combination thereof. As described, each of such materials can include coatings or layers of adhesive materials, e.g., acrylic adhesive materials, on one or more surface thereof.

Furthermore, in various instances, the gasket 320, or a portion thereof, such as a first and/or second laminated layer, does not include an acid. Also, in some versions, the gasket 320, or a portion thereof, e.g., such as a first and/or second laminated layer, is opaque and/or white. Where the gasket 320 or a portion thereof is white, the white layer provides a uniform background of optical inspection of one or more the fluidic chamber 205. In some versions, a layer, e.g., a first layer and/or second layer and/or the gasket 320, is opaque and/or a color complementary to a reaction start color, e.g., red, orange, yellow, green, blue, indigo, violet, black, gold, silver, brown, or any combination thereof. A reaction start color is the color of the reaction product and/or the optical property modifying reagent before a reaction occurs to sufficiently modify an optical property of the optical property modifying reagent to allow detection of the modified optical property indicative of the presence of a suspected analyte in the biological sample. The color complementary to a reaction start color can provide sufficient color contrast, e.g., increased color contrast as opposed to a single color, of the fluidic chamber 205 such that, for example, detection of the modified optical property can be made by a sensor.

In various instances, the gasket 320, or a portion thereof, is transparent to light, e.g., visible light. In other versions, the gasket 320, or a portion thereof, is reflective, e.g., entirely or substantially reflective to light, e.g., visible light. In other versions, the gasket 220 is substantially opaque and optically absorbing, e.g. with a black colorant. Also, as noted herein, the gasket 320 can include a first layer laminated with a second layer. In such embodiments, for example, a first layer does not include an acid and/or a second layer is opaque and/or white.

Additionally, in various instances, the gasket 320, or a portion thereof such as a sheet, has a thermal conductivity ranging from 0.1 W/m-K to 10 W/m-K, such as 0.1 W/m-K to 5 W/m-K, such as 1 W/m-K to 5 W/m-K.

According to some versions, the gasket 320 is a patterned adhesive layer. In such embodiments, the gasket 320 can be or have a portion that is porous and/or includes one or more opening extending from a first surface of the gasket 320 to a second surface of the gasket 320 opposite the first surface such that one or more contents, e.g., liquids, of a fluidic chamber 205 can pass therethrough. As such, in some aspects, one or more contents, e.g., liquids, of the fluidic chambers 205 can contact a substrate and/or one or more components thereof, e.g., a sensor and/or a heating element, directly while an assay is performed.

In addition to the gasket 320, FIG. 3A also depicts a thermal pad 325 located beneath the second piece 115. The thermal pad 325 comprises a ring shape and is configured to transfer heat from a heating element (not shown) to the plurality of fluidic chambers 205. The heat transferred by the thermal pad 325 is used to promote reactions occurring within the fluidic chambers 205. Note that in some embodiments, the thermal pad 325 is not included in the device 105. In alternative embodiments (not shown) the thermal pad 325 can be a thermal paste and/or a thermal tape.

The ring shape of the thermal pad 325 enables uniform transfer of heat to each fluidic chamber of the plurality of fluidic chambers 205. This uniform distribution of heat flux provides consistent, isothermal heating to each fluidic chamber 205, thereby standardizing the reaction conditions and enabling more accurate assays. Operation of the thermal pad 325 as well as the heating element is discussed in greater detail with regard to FIGS. 8-10B.

FIG. 3A also depicts dried or lyophilized reagents 330. As discussed with regard to FIG. 1, in some embodiments the dried or lyophilized reagents 330 are contained within each fluidic chamber 205. In some embodiments, the dried or lyophilized reagents 330 comprise assay reagents. In further embodiments, the assay reagents comprise a nucleic acid amplification enzyme and a DNA primer. In such embodiments, the assay reagents enable amplification of select nucleic acids present or suspected to be present in the biological sample. The reagents 330 are dried or lyophilized in order to prolong shelf stability of the reagents 330 and thus of the device 105. The dried or lyophilized reagents 330 located within the fluidic chambers 205 are discussed in greater detail with regard to FIG. 11.

FIG. 3B is an illustration of an underside view 300B of the uncoupled components of the device 105 for performing biological assays, in accordance with an embodiment. In other words, FIG. 3B provides an alternative view of the uncoupled components of the device 105 depicted in FIG. 3A.

FIG. 3C is an illustration of an aerial view 300C of alternative uncoupled components of the device 105 for performing biological assays, in accordance with an embodiment. Similar to FIGS. 3A and 3B, the uncoupled components of the device 105 depicted in FIG. 3C include the first piece 110, the second piece 115, the thermal pad 325, and the lyophilized reagents 330. However, instead of the gasket 320, the device 105 depicted in FIG. 3C includes a hydrophobic membrane 335.

In some embodiments, the hydrophobic membrane 335 takes the place of both the gasket 320 and the self-sealing vent material discussed with regard to the outlet vents 135. Specifically, the hydrophobic membrane 335 is operatively coupled to the first piece 110 and the second piece 115 to form fluid seals in the continuous fluidic pathways discussed with regard to FIG. 1. Furthermore, the hydrophobic membrane 335 seals the outlet vent 135 of each fluidic chamber of the plurality of fluidic chambers 205. In some embodiments, the hydrophobic membrane 335 is welded to the face of the first piece 110 shown in FIGS. 3A and 3C. In certain embodiments, the hydrophobic membrane 335 comprises polytetrafluoroethylene. The hydrophobic membrane 335 can be pre-dried to a residual moisture of between 0-0.4% w/w. Alternatively, the hydrophobic membrane 335 can be pre-dried to a residual moisture of at most 0.2% w/w. Based on this pre-drying of the hydrophobic membrane 335, the device 105 can have a shelf stability that exceeds a threshold of 12 months.

In some embodiments, energy directors (shown in FIG. 3E) serve to weld the hydrophobic membrane 335 to one of the first piece 110 and the second piece 115. In such embodiments, the energy directors are located on the face of the first piece 110 depicted in FIGS. 3B and 3D. Specifically, the energy directors are located around the fluid channels 305 and the outlet vents 135 of the first piece 110. In alternative embodiments, energy directors are not used and the hydrophobic membrane 335 is sealed in place with respect to the first piece 110 and the second piece 115 using pressure, ultrasonic welding, adhesive material, or thermal bonding.

In alternative embodiments, the device 105 may include both the gasket 220 and the hydrophobic membrane 335. For example, the gasket 220 and the hydrophobic membrane 335 may be laminated together or the hydrophobic membrane 335 may be located on a top face of the first piece 110 and the gasket 220 may be located between the first piece 110 and the second piece 115.

FIG. 3D is an illustration of an underside view 300D of the alternative uncoupled components of the device 105 for performing biological assays, in accordance with an embodiment. As shown in FIG. 3D, the hydrophobic membrane 335 has replaced the gasket 320 and the self-sealing vent material covering the outlet vents 135.

In alternative embodiments (not shown) self-sealing vents can be used to cover the outlet vents 135 without the use of the gasket 320. In such embodiments, the first piece 110 and the second piece 115 can be coupled using ultrasonic welding, adhesive, or thermal bonding.

Figure 3E:
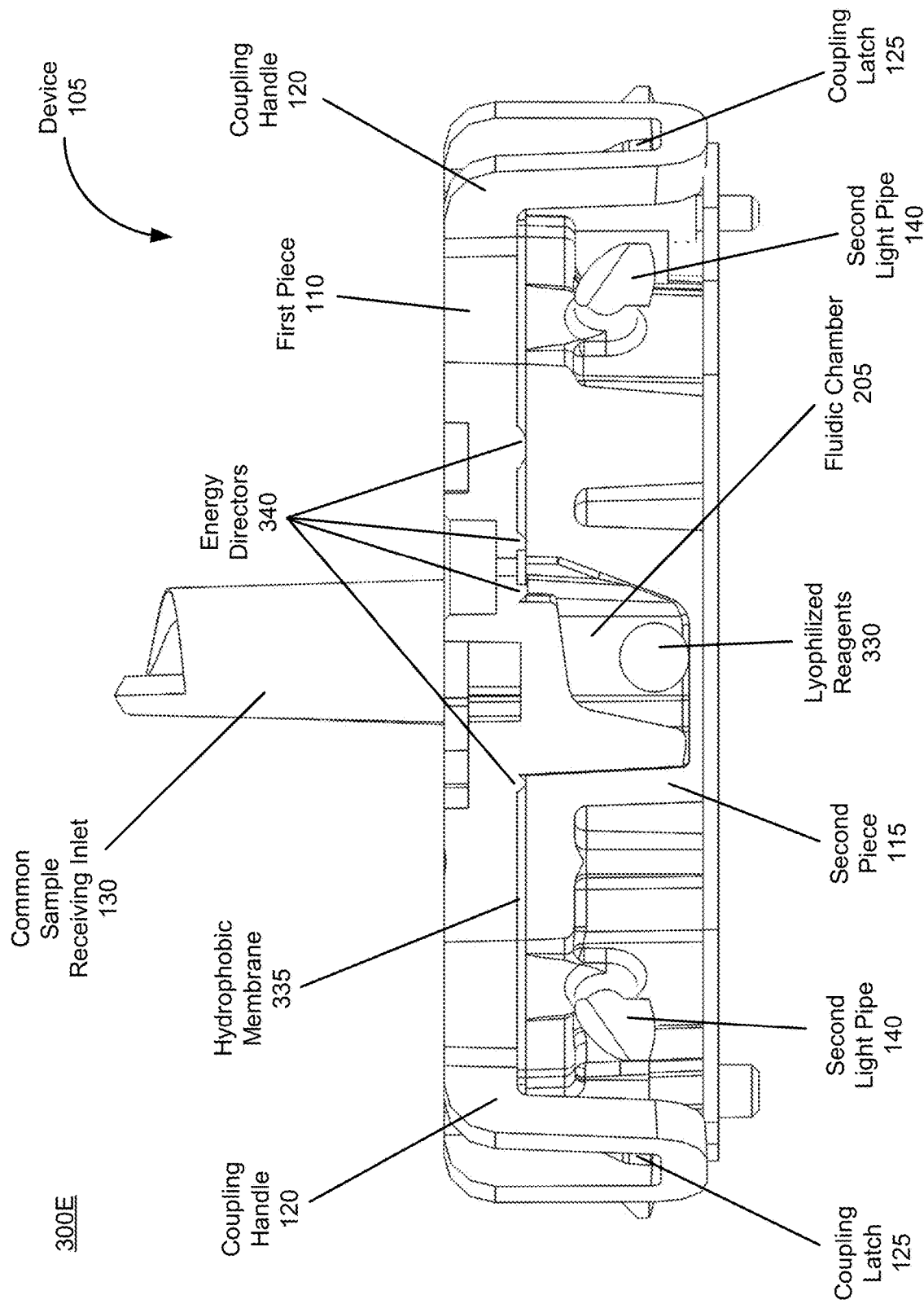
FIG. 3E is an illustration of a cross-section of the device for performing biological assays, in accordance with an embodiment.

FIG. 3E is an illustration of a cross-section 300E of the device 105 for performing biological assays, in accordance with an embodiment. Specifically, FIG. 3E depicts the first piece 110 operatively coupled to the second piece 115 by the hydrophobic membrane 335 and energy directors 340. In the embodiment depicted in FIG. 3E, the hydrophobic membrane 335 has been welded to the first piece 110 and the second piece 115 to form the plurality of continuous fluidic pathways using the energy directors 340.

Additionally, FIG. 3E depicts the lyophilized reagents 330 located within the fluidic chambers 205.

Optical Property Detection

FIG. 4 is an illustration of a cross-section of the second piece 115 of the device 105 for performing biological assays, in accordance with an embodiment. As depicted in FIG. 4, the second piece 115 of the device 105 is configured to enable detection of modified optical properties of reaction mixtures contained within the plurality of fluidic chambers 205. Specifically, the second piece 115 comprises a sensing region 215, a photosensor 405, the plurality of second light pipes 140 depicted in FIG. 1, and a plurality of first light pipes 210.

The sensing region 215 is an optical property analysis region. As described above with respect to the fluidic chambers 205, the sensing region 215 can be substantially equidistant from each of the plurality of fluidic chambers 205 in certain embodiments. In certain embodiments, this means that the sensing region 215 is located at or near a center of the device 105. In some aspects, the center region is defined with respect to the locations of the plurality of fluidic chambers 205. By locating the sensing region 215 such that it is substantially equidistant from each of fluidic chamber of the plurality of fluidic chambers 205, optical properties of the reactions mixtures contained within each fluidic chamber 205 can be accurately and precisely detected at the sensing region 215 under the same parameters. As used herein, "substantially equidistant" means that a distance of each fluidic chamber of the plurality of fluidic chambers from the single sensing region, differs from a distance of each other fluidic chamber of the plurality of fluidic chambers from the single sensing region by no more than +/−25%.

In some embodiments, the photosensor 405 is optically coupled to the first plurality of light pipes 320 and is located within the sensing region 215. The photosensor 405 detects modification of optical properties of the reactions mixtures contained within each fluidic chamber 205. For example, the photosensor 405 can be configured to detect a color change in a reaction mixture contained within a fluidic chamber 205. In an alternative embodiment, the photosensor 405 can be configured to detect an absorbance change in a reaction mixture contained within a fluidic chamber 205. The photosensor 405 can comprise one of a CMOS chip, a photodiode, a phototransistor, a photocell, and a photomultiplier tube.

To enable the photosensor 405 to detect modified optical properties of the reaction mixtures within the fluidic chambers 205, a plurality of light emitting elements 410 transmit light through the reaction mixtures within the fluidic chambers 205 and into the sensing region 215 that contains the photosensor 405. To enable this passage of light from the light emitting elements 410 to the sensing region 215 of the second piece 115, the light emitting elements 410 are located around the second piece 115 in proximity to the fluidic chambers 205 such that the fluidic chambers 205 are positioned between the light emitting elements 410 and the photosensor 405 in the sensing region 215. Specifically, each light emitting element 410 of the plurality of light emitting elements 410 is positioned to illuminate one fluidic chamber of the plurality of fluidic chambers 205. In some embodiments, the light emitting elements 410 are radially-arranged around the second piece 115 and/or around the sensing region 215. In some embodiments, the light emitting elements 410 comprise LEDs. In alternative embodiments, the light emitting elements 410 can comprise lasers.

In addition to the light emitting elements 410, the second piece 115 comprises a plurality of first light pipes 210 and a plurality of second light pipes 140 that enable the light from the light emitting elements 410 to travel to the sensing region 215. Specifically, each second light pipe of the plurality of second light pipes 140 is located between a light emitting element 410 and a fluidic chamber 205. Thus the second light pipes 140 enable light to travel from the light emitting elements 410 into the fluidic chamber 205. Additionally, each first light pipe of the plurality of first light pipes 210 is located between a fluidic chamber 205 and the sensing region 215. Thus the first light pipes 210 enable light to travel from the fluidic chambers 205 to the sensing region 215 which it is detected by the photosensor 405. For example, FIG. 4 shows light rays 415 traveling from the light emitting element 410, through the second light pipe 140, into the fluidic chamber 205, through the first light pipe 210, and into the sensing region 215 that contains the photosensor 405.

In certain embodiments, the second light pipes 140 and/or the first light pipes 210 can contain a reflecting surface 420A, a reflecting surface 420B, and/or one or more refracting surfaces (not shown) to direct the light rays 415 from the light emitting element 410, through the second light pipe 140, into the fluidic chamber 205, through the first light pipe 210, and into the sensing region 215. In certain embodiments, the reflecting surfaces 420A and 400B are oriented at 45 degree angles with respect to the normal. In alternative embodiments, the reflecting surfaces 420A and 400B can be oriented at alternative angles with respect to the normal. In even further embodiments, the reflecting surfaces 420A and 420B can be placed at alternative locations within the second light pipes 140 and the first light pipes 210 other than those depicted in FIG. 4. The refracting surfaces are discussed in greater detail with regard to FIGS. 5 and 6. In further embodiments (not shown), the first light pipes 210 and the second light pipes 140 may contain optical filters to enable wavelength selectivity.

In some embodiments, the second piece 115 or a portion thereof is transparent to light, e.g., visible light. For example, in certain embodiments, the first light pipes 210 and/or the second light pipes 140 can be transparent to visible light. As such, a user can observe an optical property modification of a sample or an aspect thereof through the second piece 115. Furthermore, transparency of the second piece 115 facilitates detection of optical properties by the photosensor 405. Examples of materials that comprise the second piece 115 and enable transparency of the second piece 115 can include polymethlamethacrylate, polystyrene, polycarbonate, polypropylene, polyethylene, polyethylene terephthalate, cyclic olefin copolymer, polyamide, and combinations thereof.

As discussed above with regard to FIGS. 1 and 2A-F, in some embodiments, each fluidic chamber 205 of the plurality of fluidic chambers is substantially equidistant from the sensing region 215. As used herein, "substantially equidistant" means that a distance of each fluidic chamber of the plurality of fluidic chambers from the single sensing region, differs from a distance of each other fluidic chamber of the plurality of fluidic chambers from the single sensing region by no more than +/−25%. Furthermore, because the first light pipes 210 are located between the fluidic chambers 205 and the sensing region 215, in such embodiments, each first light pipe of the first plurality of light pipes 210 comprise the same length between the fluidic chamber 245 and the sensing region 215. In other words, the light paths between each fluidic chamber 245 and the sensing region 215 are similar or equal in length. This similarity in light path length is advantageous because it allows the device 105 to perform multiple assays in parallel under the same specifications. This in turn allows for more accurate, controlled assay results. A preferred way of achieving this similarity in light path length is by designing the device 105 to be radially-symmetrical. In further embodiments, each first light pipe of the first plurality of light pipes 210 comprise the same dimensions. This further enables the device 105 to perform multiple controlled assays in parallel.

At least substantial radial symmetry of the device 105, including the second piece 115, enables the centralization of certain components of the device 105, which in turn enables a reduction in the quantity of those components, thereby reducing manufacturing costs for the device 105. Specifically, by placing the single photosensor 405 in the sensing region 215, the single photosensor 405 is able to detect changes in optical properties of the reaction mixtures within each fluidic chamber of the plurality of fluidic chambers 205. This use of a single, centralized photosensor 405 is advantageous because it limits the quantity of photosensors used by the device 105, thereby limiting the overall cost of the device 105. Furthermore, because photosensors are relatively expensive components compared to the other components of the second piece 115, centralization of the single photosensor 405 in the sensing region 215 is a relatively more cost-effective arrangement of the components of the second piece 115 than alternative arrangements of the second piece 115. For example, as photosensors are generally more expensive than light emitting elements 410, centralization of the single photosensor 405 in the sensing region 215 is relatively more cost-effective than centralization of a single light emitting element 410 in the sensing region 215. Furthermore, the device 105 includes no moving components and as a result is less bulky and failure prone than devices that do include moving components such as mirrors and fluidic chambers.

In addition to reducing costs by using the single photosensor 405, the first piece 110 and the second piece 115 are both monolithic pieces that are multifunctional components in that, when operatively coupled (optionally with additional components such as the gasket 220), the first piece 110 and the second piece 115 are capable of singlehandedly forming the components of the device 105 needed to perform the biological assay. Thus the simplicity and reduction in the quantity of separate components of the device 105 also reduces the overall cost of the device 105.

To use the single photosensor 405 to detect the optical properties of the plurality of reaction mixtures located in the plurality of fluidic chambers 205 via a plurality of light rays 415 originating from the plurality of light emitting elements 410, the plurality of light emitting elements 410 emit light in a repeating pattern at a specific repetition frequency such that only one of the plurality of fluidic chambers 205 is illuminated at any time. In this way, the photosensor 405 is able to detect the optical properties of each of the plurality of reaction mixtures at a different moment in time, thereby enabling accuracy of the optical property detection for each reaction mixture. Furthermore, as each of the plurality of fluidic chambers 205 is individually illuminated during each repetition of the pattern, the optical properties of each of the plurality of reaction mixtures are continuously monitored at the specific repetition frequency. In some embodiments, the repetition frequency ranges between 0.01-100 Hz. Control of the repetition frequency of the light emitting elements 410 is discussed in greater detail below with regard to FIGS. 8 and 9.

Figure 5:
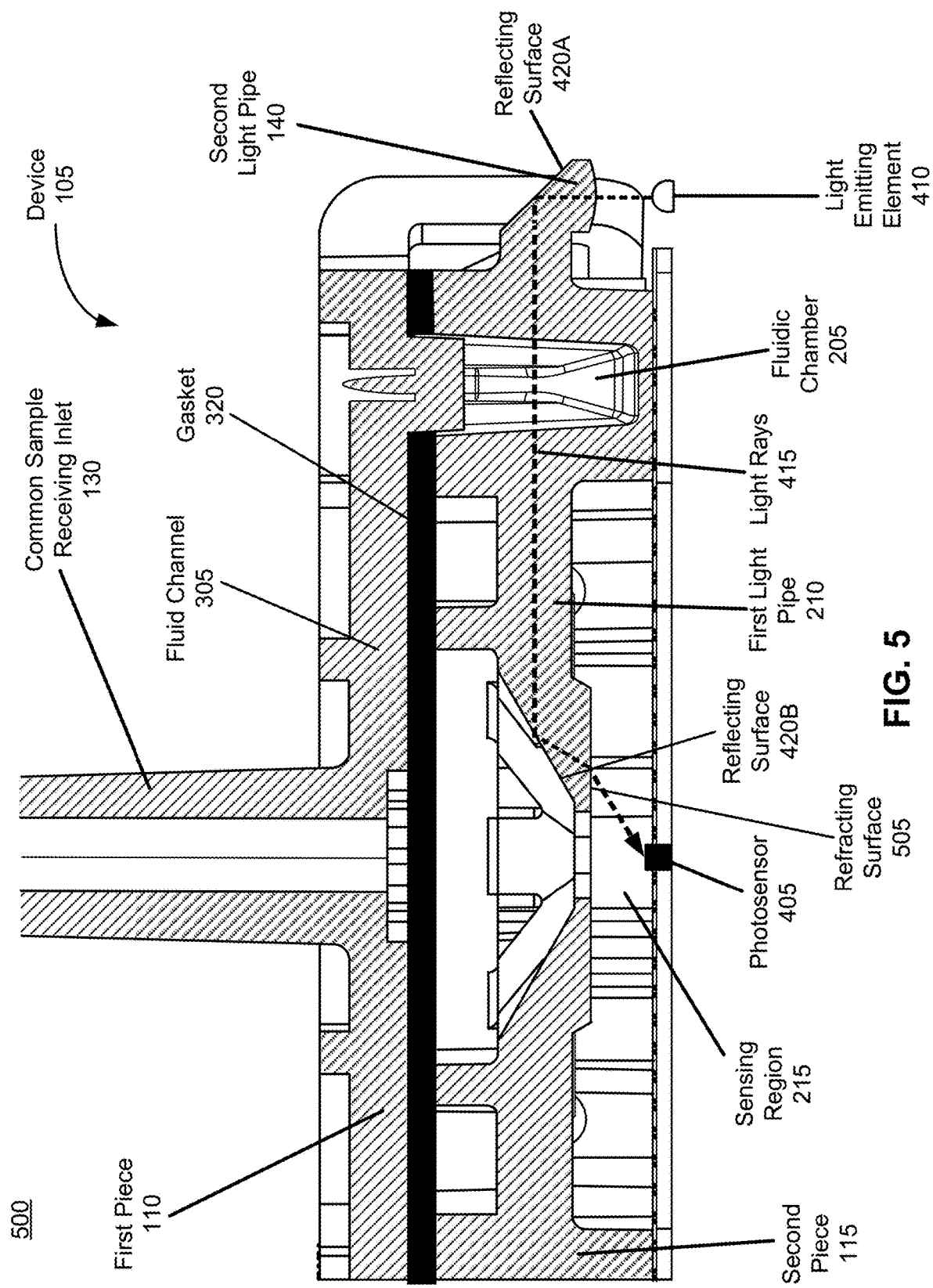
FIG. 5 is an illustration of a cross-section of the device for performing biological assays, in accordance with an embodiment.

FIG. 5 is an illustration 500 of a cross-section of the device 105 for performing biological assays 105, in accordance with an embodiment. Specifically, FIG. 5 depicts an alternative view of detection of optical properties shown in FIG. 4. Similar to FIG. 4, the reflecting surface 420A located within the second light pipe 140 and the reflecting surface 420B located within the first light pipe 210 can be used to direct the light rays 415 from the light emitting element 410 to the photosensor 405 within the sensing region 215.

FIG. 5 also depicts the refracting surface 505. The refracting surface 505 is located within the first light pipe 210, and alters the angle at which the light rays 415 enters the sensing region 215. In alternative embodiments, the refracting surface 505 can be placed at alternative locations within the first light pipe 210 other than those depicted in FIG. 4. Additionally, the refracting surface 505 can be located within the second light pipe 140 in alternative embodiments.

Figure 6:
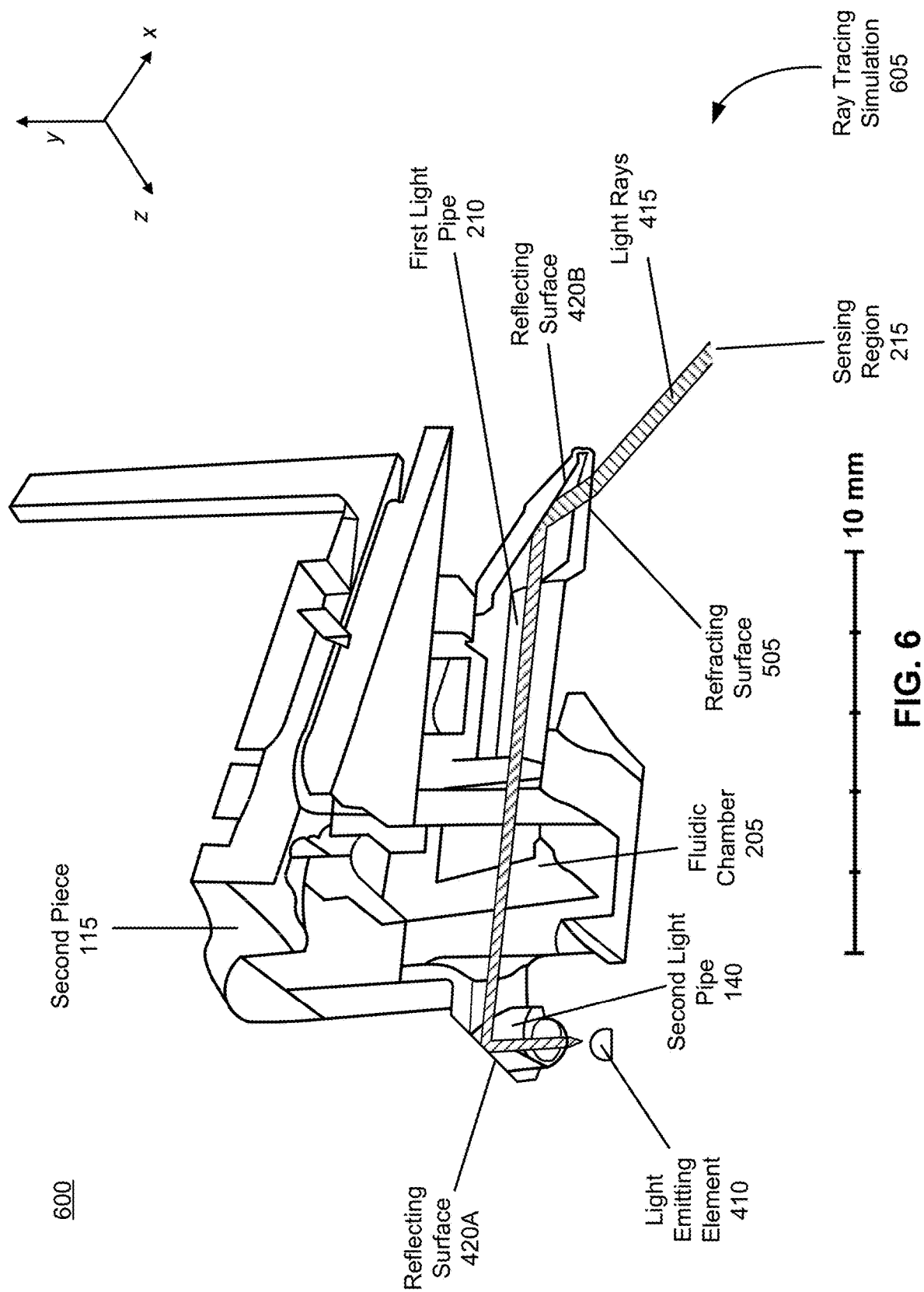
FIG. 6 is an image of a ray tracing simulation for a light ray generated by the device for performing biological assays, in accordance with an embodiment.

FIG. 6 is an image 600 of a ray tracing simulation 605 for the light rays 415. Specifically, FIG. 6 depicts the light rays 415 traveling from the light emitting element 410, through the second light pipe 140, into the fluidic chamber 205, through the first light pipe 210, and into the sensing region 215.

Note that the light rays 415 reflect and refract off of various surfaces during this process of traveling from the light emitting element 410 to the sensing region 215. For example, the light rays 415 reflect off of the reflecting surface 420A located within the second light pipe 140. In some embodiments, the reflecting surface 420A can be oriented at a 45 degree angle with respect to the normal. Additionally, the light rays 415 reflect off of the reflecting surface 420B located within the first light pipe 210. In some embodiments, the reflecting surface 420B can also be oriented at a 45 degree angle with respect to the normal.

In addition to reflecting off of the reflecting surfaces 420A and 420B, the light rays 415 can also refract off of the refracting surface 505. For example, as depicted in FIG. 6, the light rays 415 refract off of the refracting surface 505 located within the first light pipe 210 prior to entering the sensing region 215.

Figure 7:
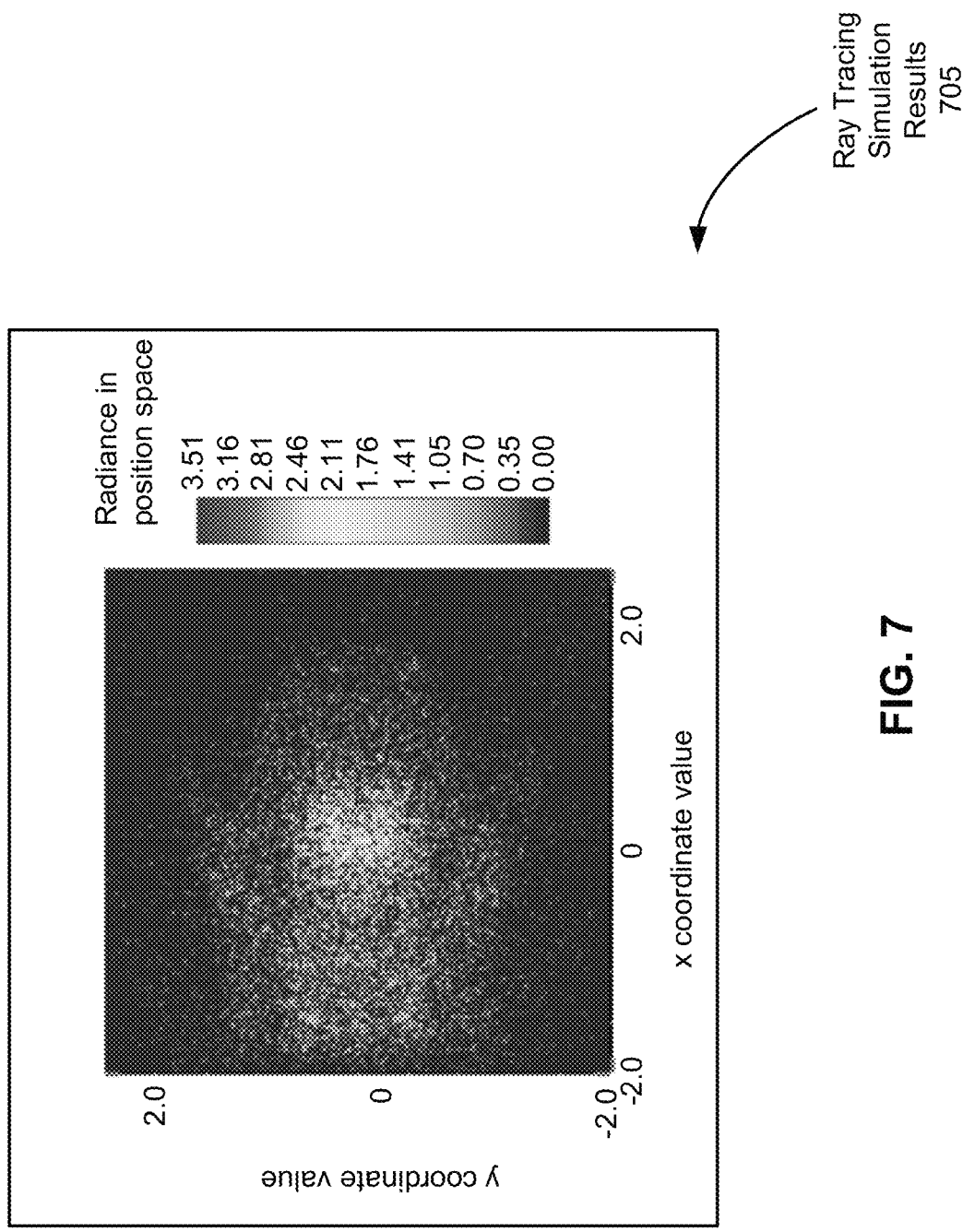
FIG. 7 is an image of ray tracing simulation results showing optical intensity at a sensing region for the ray tracing simulation of FIG. 6, in accordance with an embodiment.

FIG. 7 is an image 700 of ray tracing simulation results 705 showing optical intensity at the sensing region 215 for the ray tracing simulation 605. Specifically, FIG. 7 depicts measures of radiance across the sensing region 215. The photosensor 405 is located at or near a center of the sensing region 215. Specifically, the photosensor 405 is approximately located at coordinates of x=0, y=0. As shown in FIG. 7, the peak radiation is focused around the location of the photosensor 405 at x=0, y=0. This indicates that the light rays 415 is focused primarily at the photosensor 405, thereby enabling an accurate detection of optical properties conveyed by the light rays 415.

Systems

Figure 8:
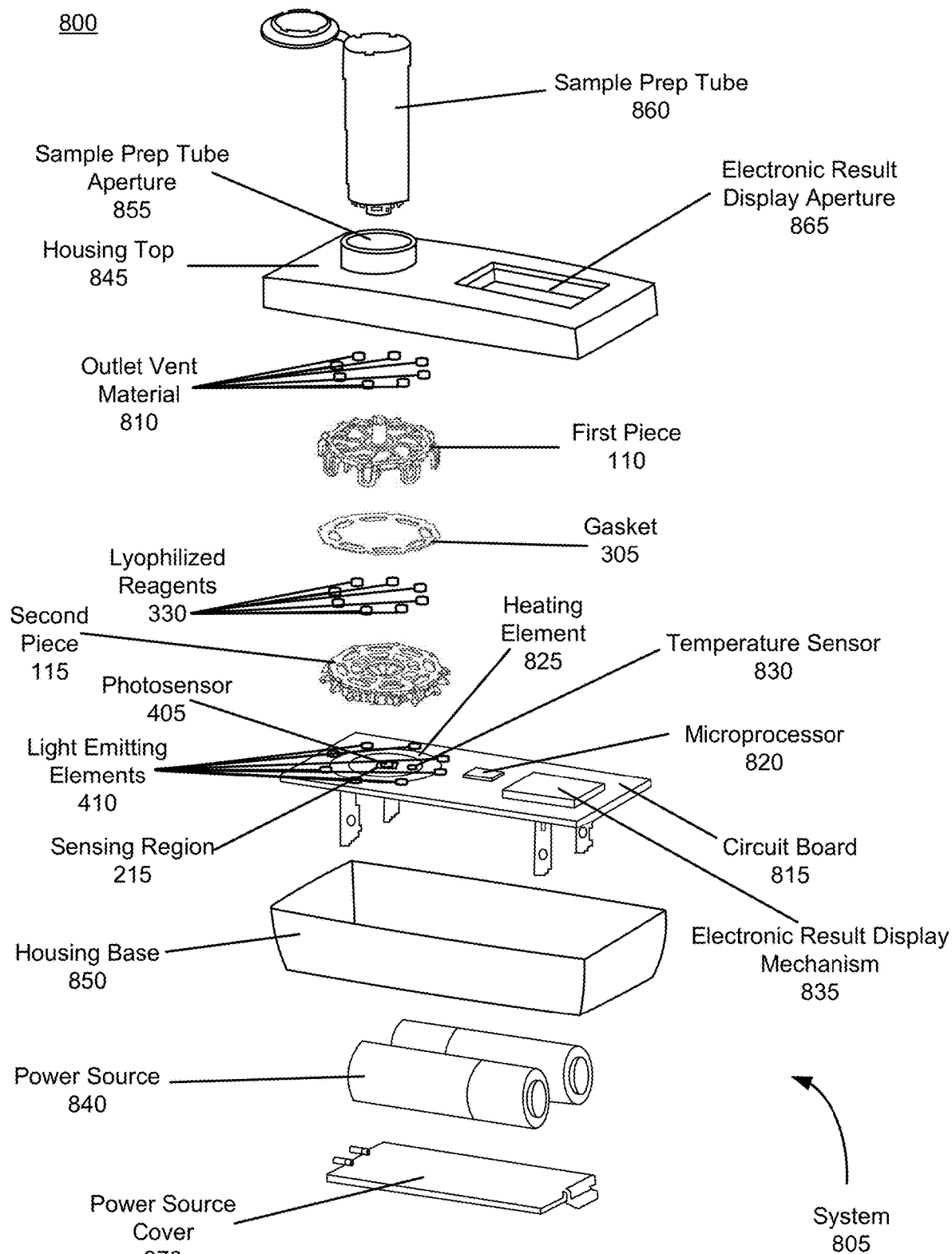
FIG. 8 is an illustration of a system for performing a biological assay, in accordance with an embodiment.

FIG. 8 is an illustration 800 of a system 805 for performing a biological assay, in accordance with an embodiment. The system 805 includes the device 105 described with regard to FIGS. 1-7 above. As discussed above with regard to FIGS. 1-7, in some embodiments, the device 105 comprises the first piece 110, the second piece 115, the gasket 320, the sensing region 215, the photosensor 405, the light emitting elements 410, outlet vent material 810 to cover the outlet vents 135 of the device 105, and lyophilized reagents 330 contained within the fluidic chambers 205. These components are depicted in FIG. 8.

In addition to the components of the device 105, the system 805 includes additional components. Specifically, the system 805 includes a circuit board 815, a microprocessor 820, a heating element 825, a temperature sensor 830, an electronic result display mechanism 835, a power source 840, a housing top 845, a housing base 850, a sample prep tube aperture 855, a sample prep tube 860, an electronic result display aperture 865, and a power source cover 870.

In some embodiments, the circuit board 815 comprises a printed circuit board, composed, for example, of a layer of fiberglass and/or copper and/or gold and/or aluminum contacts therein or thereon. For example, the circuit board 815 can be a printed circuit board composed of a layer, e.g., a fiberglass layer, having thereon metallic contacts affixed thereto with one or more adhesive, e.g., epoxy. In certain embodiments, the fluidic chambers 205 of the device 105 can be operatively coupled to the circuit board 815. For example, the device 105 can be operatively coupled to the circuit board 815 using an adhesive layer (not shown).

In certain embodiments, the microprocessor 820, the heating element 825, the temperature sensor 830, and the electronic result display mechanism 835 are also coupled to the circuit board 815. Coupling of the microprocessor 820, the heating element 825, the temperature sensor 830, and the electronic result display mechanism 835 to the circuit board 815 can comprise mechanical and/or electrical coupling.

The microprocessor 820 is configured to generate one or more outputs, e.g., electrical signals, based on one or more sets of inputs, e.g., inputs from a user and/or a sensor, and/or a timer, and/or instructions stored in a memory of the microprocessor 820. The system 805 can also include a user interface for receiving an input and operatively coupled to the microprocessor 820. The microprocessor 820 can be electrically coupled to the light emitting elements 410, the photosensor 405, the heating element 825, the temperature sensor 830, and/or the electronic result display mechanism 835. The function of the microprocessor 820 with respect to each of these components is discussed in further detail below.

Examples of such the heating element 825 include conductors which undergo resistive Joule heating, thermoelectric heat pumps such as Peltier elements, chemical heating reagents which undergo exothermic reactions, or other elements that generate heat.

The heating element 825 comprises a ring shape and is configured to heat the plurality of fluidic chambers 205 and contents thereof, to promote reactions occurring within the fluidic chambers 205. As such the heating element 825 is located beneath the second piece 115 of the device 105 such that the heating element 825 is able to transfer heat to the fluidic chambers 205. In certain embodiments, the heating element 825 is located between the circuit board 815 and the second piece 115 of the device 105. In further embodiments, the heating element 725 is a conductive trace on the circuit board 715. In other embodiments, the heating element 725 is composed of resistive elements, e.g. surface-mount resistors, affixed to the circuit board 715.

The heating element 825 can be configured to elevate the temperature of the fluidic chamber 205 and/or contents thereof, e.g., a biological sample, by 1° C. The heating element 825 can be further configured to increase the temperature of the fluidic chamber 205 and/or contents thereof from room temperature, e.g., 21° C., up to 90° C., and/or within a range of up to 90° C., in 10 minutes or less. For example, the heating element 825 can be configured to increase the temperature of the fluidic chamber 205 and/or contents thereof from room temperature to 63° C.±1° C. in 3 minutes or less and/or can be configured to maintain such a temperature for 30 minutes or more. The heating element 825 can also be configured to maintain the temperature of the fluidic chamber 205 and/or contents thereof for a period of time such as 2 hours or more or 2 hours or less. Such a temperature can be maintained at up to 90° C., and/or within a range of up to 90° C. Maintaining such a temperature is performed by applying a thermistor such as the temperature sensor 830 and/or is based on sensor feedback to the microprocessor 820 such as the microprocessor 820. The heating element 825 is configured to elevate the temperature of the fluidic chamber 205 and/or contents thereof, repeatedly, e.g., heat the contents a first time and then a second time. The heating element 825 also can heat the contents of the fluidic chamber 205 so that an optical property modification and/or nucleic acid amplification occurs. Furthermore, the heating element 825 can heat contents to perform thermo-cycling for amplification reactions, such as PCR. In those cases, it may be advantageous to configure the heating element to both heat and actively cool the reaction chambers, using a thermoelectric heat pump with reversible polarity, for example.

As discussed previously with regard to FIG. 3A, the device 105 can also include the thermal pad 325 (not shown) between the heating element 825 and the second piece 115. As noted above, the thermal pad 325 comprises a ring shape and is configured to transfer heat from the heating element 825 to the fluidic chambers 205.

Also as discussed above, the ring shape of the heating element 825 enables uniform transfer of heat to each fluidic chamber of the plurality of fluidic chambers 205. This uniform distribution of heat flux provides consistent, isothermal heating to each fluidic chamber 205, thereby standardizing the reaction conditions and enabling more accurate assays. The function of the heating element 825 is discussed in greater detail with regard to FIGS. 10A and 10B.

As mentioned above with regard to the heating element 825, the temperature sensor 830 can measure the temperature of the heating element 825, the fluidic chambers 205, and/or the contents of the fluidic chambers 205. These measurements can then be relayed to the microprocessor 820 and used by the microprocessor 820 to control the temperature of the heating element 825, and thereby the temperature of the fluidic chambers 205 and/or the contents of the fluidic chambers 205.

In some embodiments, the microprocessor 820 can be programmed to cause each of the plurality of light emitting elements 410 to emit light in the repeating pattern at the specific repetition frequency described above, wherein only one of the plurality of fluidic chambers 205 is individually illuminated at any time during the repeating pattern.

In further embodiments, the microprocessor 820 can be programmed to analyze signals received from the photosensor 405. Specifically, the microprocessor 820 can be programmed to perform an optical property modification and/or colorimetric analysis of a biological sample in the fluidic chambers 205 based on a signal received from the photosensor 405. As such, the microprocessor 820 can be configured to determine, based on input from the photosensor 405, whether a change in an optical property, e.g., color, of one or more contents of the fluidic chambers 205, has occurred.

Based on the determination, the microprocessor 205 can then generate signals to transmit to the electronic result display mechanism 835. These signals can include results of the biological assay based on the optical properties analyzed by the microprocessor 820. In some embodiments, the electronic result display mechanism 835 simply and unambiguously provides visual and/or audio results of the biological assay. In other embodiments, the result is transmitted to a receiving electronic device such as a server, personal computer, or handheld smartphone.

In some instances, the system 805 includes one or more power sources 840. The power source 840 can be operatively connected to the circuit board 815, and therefore operatively connected to any components coupled to the circuit board 815 (e.g., the photosensor 405, the light emitting elements 410, the microprocessor 820, the heating element 825, the temperature sensor 830, and the electronic result display mechanism 835). In some aspects, the power source 840 can include, for example, one or more batteries, direct current (DC) power supply, alternating current (AC) power supply, linear regulated power supply, and/or switched-mode power supply. For example, the power source 840 can, in some aspects, be one or more batteries, e.g., a portable and/or self-contained and/or replaceable battery, such as one or two AA batteries, an outlet, or another source of electrical power. The amount of power, current, and/or voltage capable of being provided by the power supply 840 can, for example, be approximately equivalent to that required to power the photosensor 405, the light emitting elements 410, the microprocessor 820, the heating element 825, the temperature sensor 830, and the electronic result display mechanism 835. In some aspects, the power source 840 can include one or more electrical cords, e.g., cords configured to operatively connect the system 805 to an outlet. Cords of the power source 840 can be configured to removably connect to the system 805 and/or the outlet.

The power source 840 is configured to turn on to provide electrical power to one component and/or to turn off to stop providing electrical power to another component. The the power source 840 can be configured to be turned on and/or off, for example, by operation of a switch, button, timer or other component operatively connected to or included in the power source 840, such as the microprocessor 820.

In certain embodiments, the device 105 (including the first piece 110, the second piece 115, the sensing region 215, photosensor 405, the light emitting elements 410, the outlet vent materials 810, and the lyophilized reagents 330), the circuit board 815 and all of the components to which the circuit board 815 is coupled (including the microprocessor 820, the heating element 825, the temperature sensor 830, and the electronic result display mechanism 835), and the power source 840 can be stored within a housing. The housing can comprise a housing top 845 that is operatively coupleable, e.g., mateable, e.g., snapedly coupleable, with a housing base 850. When operatively coupled, the housing top 845 and the housing base 850 are configured to contain, e.g., fully contain, the device 105, the circuit board 815 and all of the components to which the circuit board 815 is coupled, and the power source 840.

The housing top 845 and the housing base 850 can be composed of one or more layers of material, e.g., a polymeric material, as described herein, and can be shaped substantially as a rectangular box.

In some embodiments, the housing top 845 can include an electronic result display aperture 860. The electronic result display aperture 860 is an opening providing visual access to the electronic result display mechanism 835 such that a user of the system 805 can view signals displayed by the electronic result display mechanism 835.

In further embodiments, the housing top 845 can include a sample prep tube aperture 850. The sample prep tube aperture 850 is an opening configured to receive a sample prep tube 855. The sample prep tube aperture 850 provides access, e.g., fluidic access, to the common sample receiving inlet 130 of the device 105 such that a biological sample can be loaded into the common sample receiving inlet 130 therethrough. Specifically, the biological sample is loaded into the sample prep tube 855, passes though the sample prep tube aperture 850, and into the common sample receiving inlet 130. In certain embodiments, additional reagents can be loaded into the sample prep tube 855 aside from the biological sample. For example, an optical property modifying reagent solution comprising an optical property modifying reagent and a liquid buffer can be loaded into the sample prep tube 855 along with the biological sample. Such embodiments are discussed in greater detail below with regard to FIG. 11.

In certain embodiments, the housing base 850 comprises a power source cover 870. The power source cover 850 is configured to protect and provide access to the power source 840.

According to some embodiments, the system 805 and components thereof, are hand-held devices or components. As used herein, the term "hand-held" refers to the characteristic ability of an aspect to be held (e.g., retained, or easily or comfortably held) in a hand, such as the hand of a mammal, such as the hand of a human, such as the hand of an adult male or female human of an average size and/or strength. As such, a hand-held aspect is an aspect that is sized and/or shaped to be retained (e.g., easily or comfortably retained) in the hand of a human. A hand-held aspect can also be an aspect that can be moved (e.g., easily moved, such as easily moved in a vertical and/or horizontal direction) by a human (e.g., one or two hands of a human).

In the ideal case, the system 805 is inexpensive enough to be disposable, simplifying use and eliminating the need for maintenance and cleaning.

Figure 9:
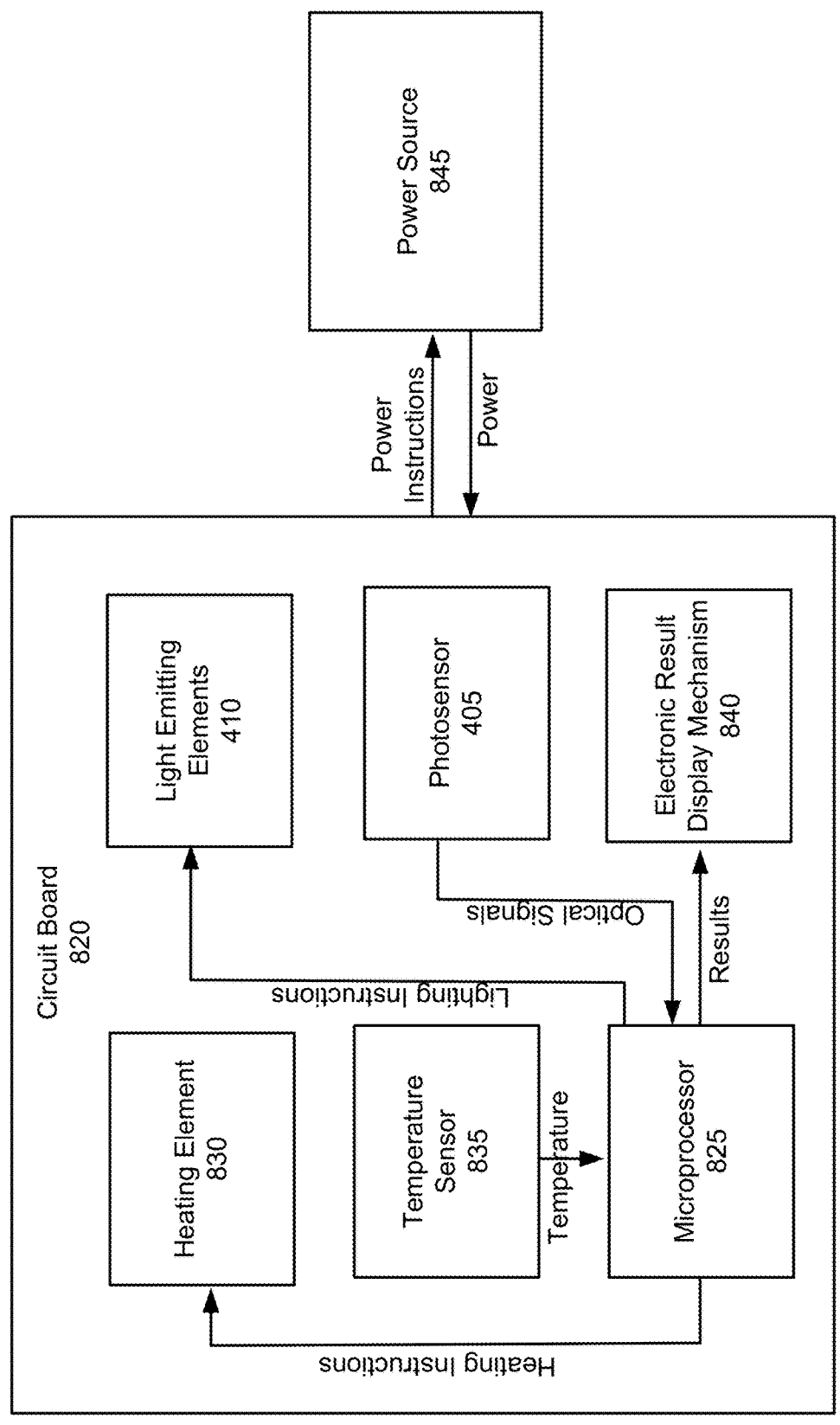
FIG. 9 is a block diagram depicting interactions between powered components of the system for performing a biological assay, in accordance with an embodiment.

FIG. 9 is a block diagram 900 depicting interactions between powered components of the system 805, in accordance with an embodiment. Specifically, FIG. 9 depicts interactions between the power source 840 and components of the system 805 that are powered by the power source 840. In the embodiment depicted in FIG. 9, the circuit board 815, and the components coupled to the circuit board 815, are powered by the power source 840. As shown in FIG. 9, the components coupled to the circuit board 815 include the photosensor 405, the light emitting elements 410, the microprocessor 820, the heating element 825, the temperature sensor 830, and the electronic result display mechanism 835. In alternative embodiments, alternative components can be coupled to the circuit board 815. For example, in certain embodiments, the temperature sensor 825 and/or the electronic result display mechanism 835 can not be coupled to the circuit board 815.

The power source 840 provides power to the circuit board 815. This power is transferred from the circuit board 815 to the components coupled to the circuit board 815. For example, the power is transferred from the circuit board 815 to the photosensor 405, the light emitting elements 410, the microprocessor 820, the heating element 825, the temperature sensor 830, and/or the electronic result display mechanism 835. The microprocessor 820 in turn provides instructions to the power source 840 regarding the specifications of the power needed to operate the components coupled to the circuit board 815 at a particular instant in time.

The microprocessor 820 also provides operational instructions to certain components coupled to the circuit board 815. For example, the microprocessor 820 provides heating instructions to the heating element 825. The heating instructions detail specifications of the heat needed to heat the contents of the fluidic chambers 205 based on a specified heating protocol. In certain embodiments, the heating instructions provided to the heating element 825 by the microprocessor 820 can be based on temperature information obtained by the temperature sensor 830 and passed to the microprocessor 820.

The microprocessor 820 can also provide lighting instructions to each light emitting element of the plurality of light emitting elements 410. The lighting instructions can detail the repeating pattern in which the light emitting elements 410 light up and/or the repetition frequency of the repeating pattern.

The photosensor 405 can use the light emitted by the light emitting elements 410 to capture optical information about the contents contained within the fluidic chambers 205. For example, optical information can include information about the optical properties of the contents contained within the fluidic chambers 205. This optical information can then be sent to the microprocessor 820. The microprocessor 820 analyzes these optical signals and generates one or more results of the assay. These results can be sent by the microprocessor 820 to the electronic result display mechanism 835 where they are simply and unambiguously provided to the user of the system 805.

Figure 10B:
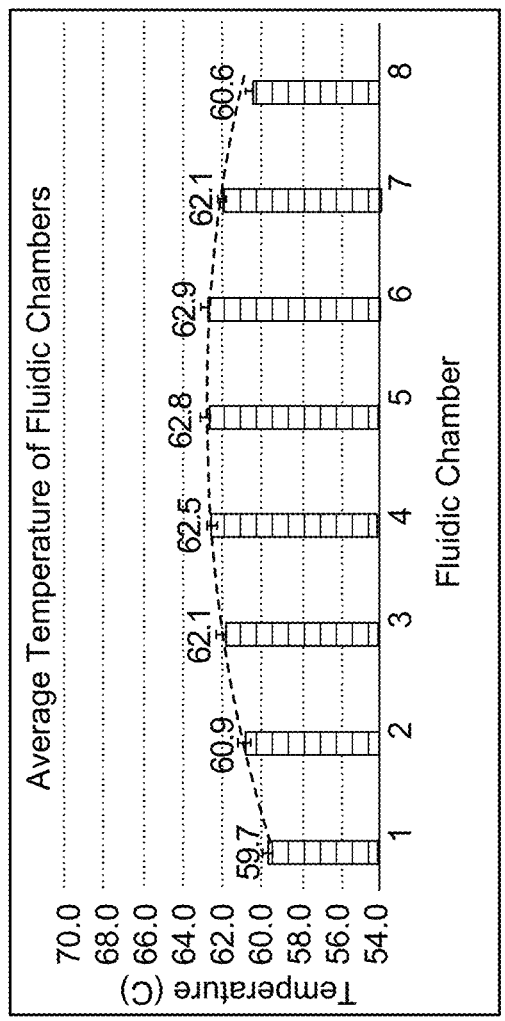
FIG. 10B is a bar graph depicting average temperature measurements for each of a plurality of fluidic chambers of the system for performing biological assays when heated by the heating element, in accordance with an embodiment.
Figure 10A:
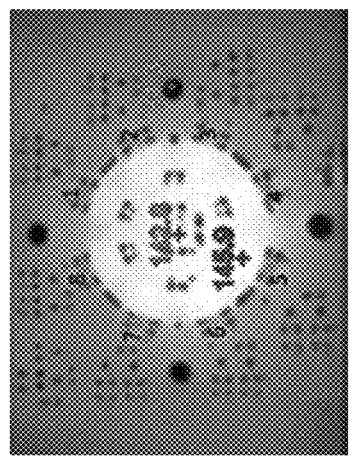
FIG. 10A is a thermal image of a heating element of the system for performing a biological assay, in accordance with an embodiment.

FIG. 10A is a thermal image 1000A of the heating element 825, in accordance with an embodiment. As described above with regard to FIGS. 3A, 3B, and 8, the heating element 825 comprises a ring shape such that the contents of each fluidic chamber of the plurality of fluidic chambers 205 can receive uniform heat flux from the heating element 825. As shown in FIG. 10A, the temperature of the heating element 825 is relatively uniform throughout the area covered by the heating element 825.

FIG. 10B is a bar graph 1000B depicting average temperature measurements for each of the plurality of fluidic chambers 205 when heated by the heating element 825, in accordance with an embodiment. Specifically, the bar graph 1000B demonstrates that the average temperature for each fluidic chamber 205 is similar. For example, the average temperature for the plurality of fluidic chambers 205 ranges from 59.7 degrees Celsius to 62.9 degrees Celsius. Thus, the average temperature for each fluidic chamber of the plurality of fluidic chambers 205 is relatively uniform.

Methods

The present disclosure includes methods of modifying an optical property in a biological sample assay. Such a modification can be performed on a biological sample, or an aspect associated therewith, such as a reaction mixture or a reaction product. Where desired, modification of an optical property can be performed with a biological sample assay optical property modifying device and/or system as such the device 105 and the system 805 described herein.

Figure 11:
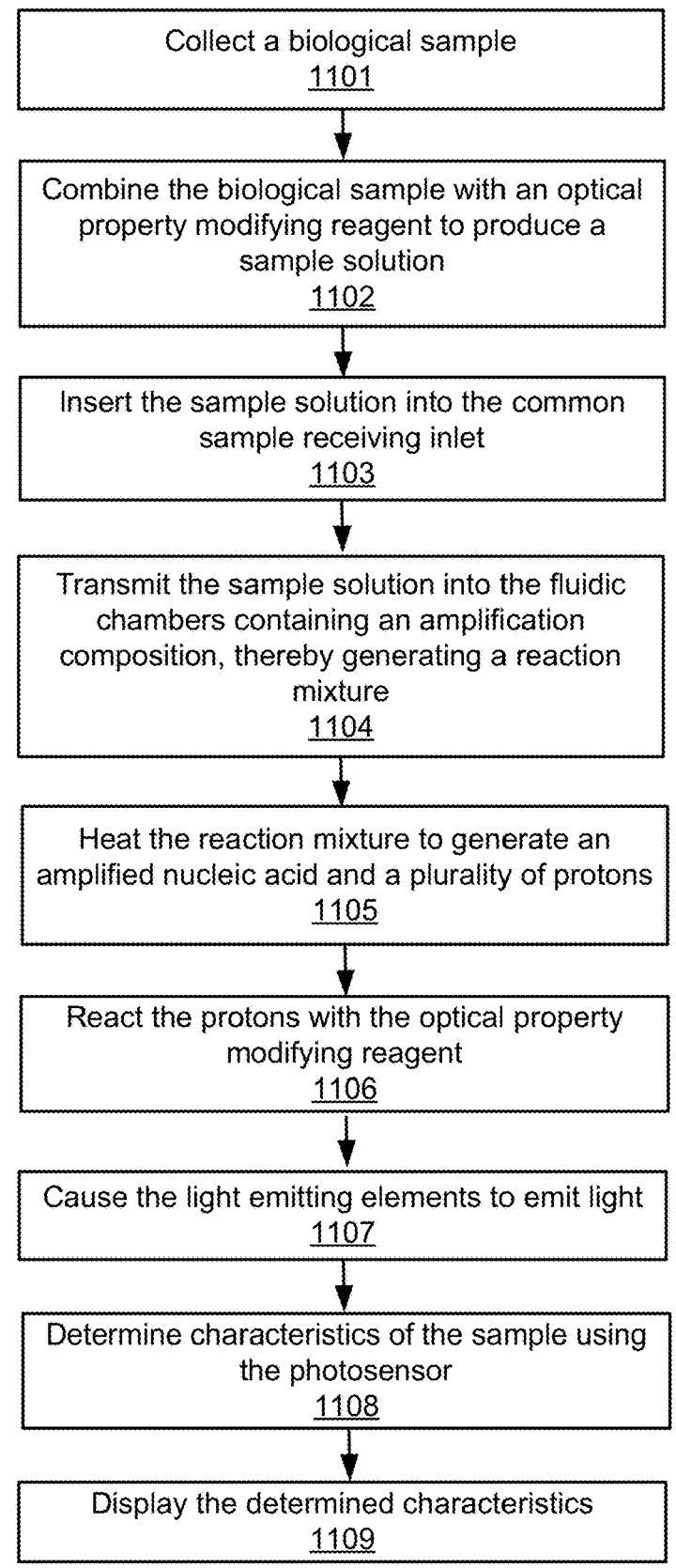
FIG. 11 is a flow chart of a method for performing a biological assay using the system for performing a biological assay, in accordance with an embodiment.

FIG. 11 is a flow chart of a method 1100 for performing a biological assay using the system 805, in accordance with an embodiment. In other embodiments, the method can include different and/or additional steps than those shown in FIG. 11. Additionally, steps of the method can be performed in different orders than the order described in conjunction with FIG. 11 in various embodiments.

A subject provides 1101 a biological sample. As described above with regard to FIG. 1, the biological sample is a sample containing a quantity of organic material, e.g., one or more organic molecules, such as one or more nucleic acids e.g., DNA and/or RNA or portions thereof, which can be taken from the subject. In some aspects, the biological sample is a nucleic acid amplification sample, which is a sample suspected of including one or more nucleic acids or portions thereof which can be amplified.

The provided biological sample can include one or more cells, such as tissue cells of the subject. As used herein, the term "tissue" refers to one or more aggregates of cells in a subject (e.g., a living organism, such as a mammal, such as a human) that have a similar function and structure or to a plurality of different types of such aggregates. Tissue can include, for example, organ tissue, muscle tissue (e.g., cardiac muscle; smooth muscle; and/or skeletal muscle), connective tissue, nervous tissue and/or epithelial tissue. Tissue can, in some versions, include cells from the inside of the subject's cheek and/or cells in the subject's saliva.

The provided biological sample can include, for example, human saliva, urine, human mucus, blood, or a solid tissue such as buccal tissue. The biological sample can also include bacteria or spores. The biological sample can be provided by a sample collector. Providing can include contacting, e.g., rubbing and/or scraping, the sample collector against one or more surfaces of the subject and/or surfaces of the biological sample of the subject, such as a liquid, e.g., saliva and/or blood, sample extracted from the subject. As such, in some versions, providing includes extracting one or more biological samples from the subject. In some versions, providing the biological sample can include instructing the subject to produce the biological sample, such as by spitting onto and/or into the sample collector. Providing the biological sample can also include retaining the biological sample or a portion thereof, e.g., one or more cells, on the sample collector while, for example transferring the sample collector to the device 105. In some instances, the sample collector is a swab and providing the biological sample includes swabbing the inside of the subject's mouth and/or nose to obtain the biological sample on the collector. In some versions, sample collectors are nasopharyngeal, mid-turbinate, genital, and/or nasal swabs. After the biological sample is provided, the method 1100 can include processing the biological sample so that it is a prepared biological sample.

A prepared biological assay sample is a biological sample which has been processed for example by exposing the sample to a preparation solution, such as a solution including a lysing agent, such as a detergent. Accordingly, in some embodiments, the biological sample is a lysate. Such preparation can enable the prepared biological sample to react, for example, with assay reagents and/or an optical property modifying reagent upon exposure thereto. The exposure can include lysing cells of the sample with a lysing agent of the preparation solution and/or extracting nucleic acids therefrom. Such extracted nucleic acids can be released into the resulting prepared sample solution. In some embodiments, a step of extracting genomic deoxyribonucleic acid (DNA) from the biological sample is included.

The user of the system 805 combines 1102 the provided biological sample with an optical property modifying reagent solution to product a sample solution. In some embodiments, the optical property modifying reagent solution comprises an optical property modifying reagent and a liquid buffer.

Optical property modifying reagents can include, for example, pH sensitive dyes, fluorescent dyes, FRET dyes, micro and nano particles, fluorescent proteins, colorimetric substrates, enzymes and reagents, plasmonic structures, precipitation reagents and substrates, or any combination thereof.

In some versions, the optical property modifying reagent is or includes an enzyme-linked immunosorbent assay (ELISA) reagent. In some aspects, the ELISA reagent is selected from the group consisting of alkaline phosphatase, horseradish peroxidase, β-galactosidase, BCIP/NBT (5-bromo-4-chloro-3-indolyl-phosphate/nitrobluetetrazolium), TMB (3,3',5,5' tetramethylbenzidine), DAB (3,3',4,4' diaminobenzidine), 4CN (4-chloro-1-naphthol). TMB (dual function substrate), ABTS (2,2'-azino-di [3-ethylbenzthiazoline] sulfonate), OPD (o-phenylenediamine), MUG (4-methylumbelliferyl galactoside), HPA (hydroxyphenylacetic acid), and HPPA (3-p-hydroxyphenylproprionic acid).

Optical property modifying reagents, in various instances, can include one or more optical property modifying substances and as such, be configured to have one of their optical properties, such as color, modified. As such, the method 1100 includes modifying one or more optical properties of an optical property modifying reagent.

Modifying an optical property refers to changing one or more optically-recognizable characteristics of an aspect, e.g., a sample, such as a characteristic resulting from wavelength and/or frequency of radiation, e.g., light, emitted from an aspect, such as color, fluorescence, phosphorescence, etc. For example, in some versions, the optical property is color and modifying the optical property includes changing the color. In some aspects, such an optical property modification, e.g., color change, is detectable by an unassisted human eye under, for example ambient light. In alternative aspects, such as the method 1100, the optical property modification is detectable using a photosensor such as the photosensor 405. Modifying an optical property can also include changing the transmittance and/or opacity of a substance and can include causing the substance to change substantially from transparent to opaque or from opaque to transparent. As such, the method 1100 can include detecting such a change in transmittance with the photosensor 405.

The user inserts 1103 the sample solution into the common sample receiving inlet 130 of the device 105 of the system 805. As described with regard to FIG. 8, inserting 1103 the sample solution into the common sample receiving inlet 103 can further comprise inserting the sample solution into the sample prep tube 855 of the system 805.

The system 805 transmits 1104 the sample solution into the fluidic chambers 205. Specifically, the system 805 transmits 1104 a portion of the sample solution out of the common sample receiving inlet 130, into the plurality of extending fluid channels 305, out of the termini of the plurality of fluid channels 310, and into the fluid inlets 315 of the plurality of fluidic chambers 205, wherein the fluidic chambers 205 comprise assay reagents, thereby generating a nucleic acid reaction mixture.

Transmitting the sample solution can include moving, e.g., flowing, the sample solution, to one or more fluidic chambers of the plurality of fluidic chambers 205. Such flowing can include biasing, e.g., pumping, the sample solution to move through the fluid channels 310. Because the common sample receiving inlet 130 is substantially equi-distant from each of the plurality of fluidic chambers 205, the distances traveled by the sample solution from the common sample receiving inlet 130 to each fluidic chamber 205 are approximately equal. And thus the amounts of time that the sample solution takes to travel from the common sample receiving inlet 130 to each fluidic chamber 205 are approximately equal. This enables the system 805 to perform multiple, controlled assays in parallel.

As noted above, in some embodiments, each of the fluidic chambers 205 comprises assay reagents. As such, transmitting the sample solution into one or more of the fluidic chambers 205 can include mixing the sample solution with the assay reagents, and thereby generating the nucleic acid reaction mixture including the sample solution and the assay reagents for carrying out a nucleic acid amplification reaction.

The assay reagents comprise enzymes and nucleic acid primers capable of reacting with a biological sample such that one or more nucleic acids suspected to be present within the sample can be amplified, if present, e.g., amplified isothermally. In certain embodiments, the assay reagents comprises nucleic acid amplification enzymes and DNA primers. For example, the assay reagent can include one or more primers, deoxynucleotides (dNTPs), and/or polymerases, Trizma pre-set crystals (Tris buffer, pH 8.8; Sigma, cat. no. T9443), Potassium chloride (KCl; Wako Pure Chemicals, cat. no. 163-03545), Magnesium sulfate heptahydrate (MgSO4; Wako Pure Chemicals, cat. no. 137-00402), Ammonium sulfate ((NH4)2SO4; Kanto Chemical, cat. no. 01322-00), Tween 20 (Tokyo Chemical Industry, cat. no. T0543), Betaine solution (Betaine, 5 M; Sigma, cat. no. B0400), Calcein (DOJINDO, cat. no. 340-00433) plus one or more optical modification reagents as discussed above, Manganese(II) chloride tetrahydrate (MnCl2; Wako Pure Chemicals, cat. no. 133-00820), Agarose S, EtBr solution, template nucleic acids, or any combination thereof. In addition, in some versions, the assay reagents, can be stored in the fluidic chambers 205 in dry, e.g., lyophilized, form. As such, preparing the reaction mixture can include mixing the sample solution and the assay reagents and/or hydrating the assay reagent.

The assay reagents can comprise one or more reagents capable of amplifying nucleic acids present in a biological sample via an isothermal amplification protocol including: transcription mediated amplification, strand displacement amplification, nucleic acid sequence-based amplification, rolling circle amplification, loop-mediated isothermal amplification, isothermal multiple displacement amplification, helicase-dependent amplification, circular helicase-dependent amplification, single primer isothermal amplification, loop-mediated amplification, or any combination thereof.

In certain embodiments, the amplification reaction performed is LAMP. In a LAMP reaction, a double- or single-stranded DNA template in dynamic equilibrium at an elevated temperature is amplified using two or three pairs of primers. The primers are designed based on the DNA template, using primer design software such as LAMP Designer (Premier Biosoft, Palo Alto, Calif.). In the first step of the LAMP reaction, the F2 region of the FIP (Forward Inner Primer) anneals to the single stranded DNA at the respective complementary (F2c) position. Next, a polymerase with strand displacement activity incorporates dNTPs along the template from the 3' end of F2. The incorporation of nucleotides releases protons, reducing the pH of the reaction mix. Then, the F3 forward primer anneals to the F3c region upstream of the F2 region and on the template. The F3 forward primer begins amplifying the template strand, which releases further protons and displaces the FIP-incorporated strand that was synthesized previously. This single strand contains an F1 sequence (within the target sequence) along with its complementary F1c sequence (within the FIP). This forms a stem-loop as F1c anneals to F1 at the 5' end. At the same time, the BIP (Backward Inner Primer) anneals to the other end of the strand and nucleotides extend from B2, releasing more protons. The backward primer B3 then binds to the B3c region, downstream of the B2 region, displaces the BIP-amplified strands and promotes extension to create the double strand. This displaced strand now contains a B1 sequence (within the target sequence) along with its complementary B1c sequence (within the BIP), forming another stem loop in the 3' end. The structure now has two stem-loop structures at each end from which continuous displacement and extension occur to amplify the template. The LAMP reaction can be amplified by adding further Forward and Backward Loop primers to produce more amplicons with stem loop structures.

The LAMP procedure can take place at a fixed temperature, minimizing the need for any expensive thermocycling equipment. Typically, isothermal methods require a set temperature, which is determined by the selected reagents. For example, enzymes function best between 60-65° C. in LAMP methods. Amplification according to the subject embodiments can also be performed by applying PCR.

In some embodiments, the system 805 heats 1105 the reaction mixture to generate an amplified nucleic acid and a plurality of protons. Specifically, heating the reaction mixture with the heating element 825 promotes a nucleic acid amplification reaction using the nucleic acid from the biological sample and the assay reagents. This reaction generates the amplified nucleic acid and the plurality of protons.

In some embodiments, the heating step 1105 includes transferring thermal energy from the heating element 825 to the thermal pad 325 to one or more of the fluidic chambers 205. Heating the reaction mixture promotes the nucleic acid amplification reaction between, the nucleic acids of the biological sample and the assay reagent. This nucleic acid amplification reaction generates the amplified nucleic acid and the plurality of protons.

The protons then react 1106 with the optical property modifying reagent. Reacting the reaction product, or an aspect thereof, with an optical property modifying reagent can include chemically modifying the reaction product and/or the optical property modifying reagent, such as by bonding the one or more protons to the optical property modifying reagent. In some embodiments, this reacting of the protons with the optical property modifying reagent sufficiently modifies an optical property of the optical property modifying reagent to allow detection of the modified optical property indicative of the presence of a suspected analyte in the biological sample.

The system 805 causes 1107 the light emitting elements 410 to emit light. Specifically, the microprocessor 820 of the system 805 instructs the plurality of light emitting elements 410 to emit light in a repeating pattern at a repetition frequency. During the repeating pattern, each light emitting element of the plurality of light emitting elements 410 emits light at a distinct time point such that only one of the plurality of fluidic chambers 205 is illuminated at any time. Exposure to light can provide a change in conditions such that optical properties can be measured. In this way, during each repeating pattern, optical properties of the contents of each fluidic chamber 205 can be continuously monitored by the photosensor 405.

Based on the optical properties detected in step 1107, the system 805 determines 1108 one or more characteristics of the samples contained in the fluidic chambers 205. To determine the one or more characteristics of the samples, the photosensor 405 sends information about the detected optical properties to the microprocessor 820, and the microprocessor 820 analyzes this information. Specifically, the microprocessor 820 can perform an optical property analysis of the reaction mixtures in the one or more the fluidic chambers 205. Performing the optical property analysis can include determining whether a change in an optical property of one or more contents of the fluidic chambers 205 has occurred.

Optical property analysis can be performed in real-time throughout the amplification reaction described with regard to step 1105, or after the performance of the amplification reaction. Detection of the modified optical properties of the reaction mixture can be associated with a digital indication of a presence or absence of the amplification reaction product. In other words, detection of the modified optical property of the reaction mixture can provide information regarding whether the amplification reaction product is present or absent. In certain embodiments, detection of a modified optical property of the reaction mixture indicates that the exponential or plateau phase of the amplification reaction has been obtained.

In some embodiments, detection of the amplification reaction product is accelerated relative to an amplification reaction that uses a reaction mixture without a halochromic agent. In further embodiments, the optical property modification of the reaction mixture is detected in less than 60 minutes from a starting time of the amplification reaction. Accelerated detection of the amplification reaction product is obtained because the halochromic agent (a weak acid or base) in the reaction mixture absorbs protons generated during the amplification reaction, and recombination of the free protons acts to accelerate the detection of the amplification reaction. The reaction can be designed so that minimal amplification is required to generate a pH transition sufficient for the halochromic agent to change optical property. Conventional amplification techniques that use fluorescent intercalating dyes, molecular beacons, hybridization probes, dye-based detection, UV-Vis, or other detection methods require a certain threshold amount of amplification to occur before an amplification signal is detectable. However, the methods of the present invention require a relatively smaller threshold amount of amplification before an optical property modification of the halochromic agent is detectable, and therefore the detection of an amplification reaction product is accelerated relative to conventional amplification methods.

The system 805 displays 1109 the determined characteristics using the electronic result display mechanism 835. Specifically, the microprocessor 820 transmits a signal comprising the determined characteristics to the electronic result display mechanism 835, where the results are simply and unambiguously provided to the user of the system 805. As noted above, the results provided can be in the form of a visual output on a display and/or in the form of an audio output.

Of note with regard to the method 1100 is that in various embodiments, the system 805 comprises one or more, e.g., three, assay controls: a sample adequacy control, a positive control, e.g., an internal positive control, and/or a negative control. The sample adequacy control detects, for example, abundant human nucleic acid markers such as housekeeping genes, RNA, and/or human β-actin deoxyribonucleic acid (DNA) to ensure a sufficient swab sample was provided. The positive control amplifies a synthetic oligonucleotide that can be co-packaged and/or co-lyophilized within the fluidic chambers 205. Such a synthetic oligonucleotide can be included, for example, in the optical property modifying reagent solution and/or in the assay reagents. Such a control ensures that the system 805 operates under conditions that allow amplification of genetic markers of interest. The negative control also amplifies the positive control but without the co-lyophilized synthetic oligonucleotide. Such a control ensures the absence of any contaminating self-amplifying amplicon.

Examples

Figure 12:
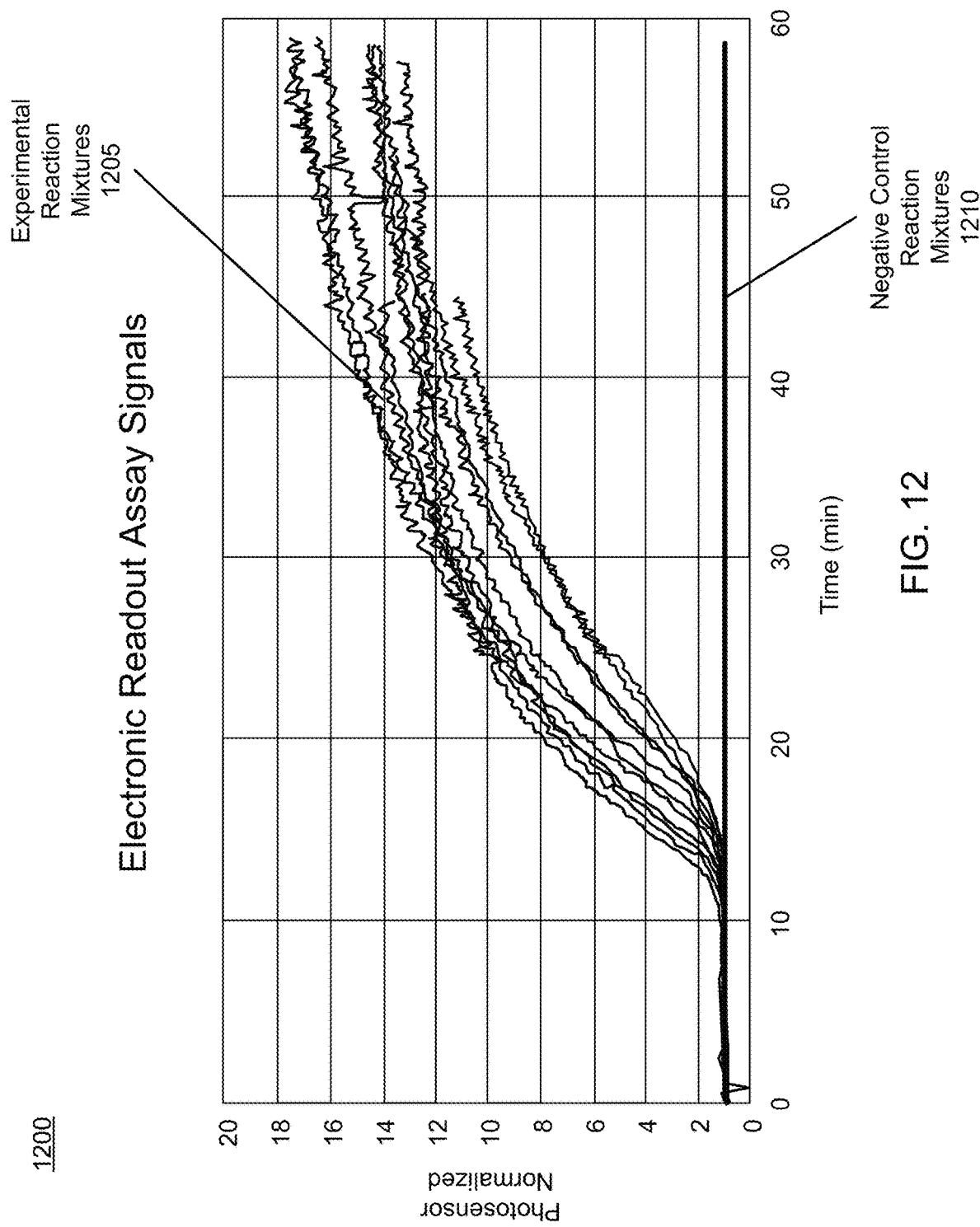
FIG. 12 is a line graph depicting optical absorbance signals detected by a photosensor of the system for performing a biological assay over time for a plurality of reaction mixtures contained within the plurality of fluidic chambers of the system, in accordance with an embodiment.

FIG. 12 is a line graph 1200 depicting optical absorbance signals detected by the photosensor 405 over time for a plurality of reaction mixtures contained within the plurality of fluidic chambers 205, in accordance with an embodiment. A first subset of the fluidic chambers 205 comprise an experimental reaction mixture 1305, and a second subset of the fluidic chambers 205 comprise a negative control mixture 1310. In the example provided in FIG. 12, the experimental reaction mixture 1305 contains a biological sample containing a target nucleic acid, an optical property modifying reagent solution, and assay reagents. Furthermore, in this example, amplification of the target nucleic acid is expected to result in a reduction in optical absorbance. The negative control reaction mixture 1310 contains an identical solution which is lacking the target nucleic acid.

As seen in FIG. 12, the fluidic chambers 205 comprising the experimental reaction mixture 1305 show an increase in light detected by the photosensor 405 over time, as the amplification reaction proceeds. In other words, as the amplification reaction proceeds, the fluidic chambers 205 comprising the experimental reaction mixture 1305 display a reduction in optical absorbance. This reduction in optical absorbance indicates the increasing presence of the target nucleic acid within the reaction mixture 1305.

On the other hand, the fluidic chambers 205 comprising the negative control reaction mixture 1310 show no increase in light detected by the photosensor 405 over time, as the amplification reaction proceeds. In other words, as the amplification reaction proceeds, the fluidic chambers 205 comprising the negative control reaction mixture 1310 display no reduction in optical absorbance. This lack of reduction in optical absorbance indicates the absence of the target nucleic acid within the reaction mixture 1310.

Note that the experiment depicted in FIG. 12 was set up such that the fluidic chambers 205 in which the experimental reaction mixtures 1305 and the negative control reaction mixtures 1310 were placed are alternating. In other words, each fluidic chamber 205 that contains the experimental reaction mixture 1305 is located between two fluidic chambers 205 that contain the negative control reaction mixture 1310, and each fluidic chamber 205 that contains the negative control reaction mixture 1310 is located between two fluidic chambers 205 that contain the experimental reaction mixture 1305. This layout and the resulting data both expected and realized in the graph 1200, indicate that the system 805, and more specifically, the device 105 on which the assay was performed, demonstrate limited crosstalk between neighboring fluidic chambers 205. Specifically, the graph 1200 indicates that the optical signals transmitted through the first light pipes 210 and the second light pipes 140 are transmitted without interference from optical signals traveling through neighboring light pipes.

Upon reading this disclosure, those of skill in the art will appreciate still additional alternative structural and functional designs through the disclosed principles herein. Thus, while particular embodiments and applications have been illustrated and described, it is to be understood that the disclosed embodiments are not limited to the precise construction and components disclosed herein. Various modifications, changes and variations, which will be apparent to those skilled in the art, can be made in the arrangement, operation and details of the method and apparatus disclosed herein without departing from the spirit and scope defined in the appended claims.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments can be described using the expression "coupled" and "connected" along with their derivatives. For example, some embodiments can be described using the term "coupled" to indicate that two or more elements are in direct physical or electrical contact. The term "coupled," however, can also mean that two or more elements are not in direct contact with each other, but yet still co-operate or interact with each other. The embodiments are not limited in this context unless otherwise explicitly stated.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but can include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the invention. This description should be read to include one or at least one and the singular also includes the plural unless it is obvious that it is meant otherwise.

Some portions of this description describe the embodiments of the invention in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. Furthermore, it has also proven convenient at times, to refer to these arrangements of operations as modules, without loss of generality. The described operations and their associated modules can be embodied in software, firmware, hardware, or any combinations thereof.

Any of the steps, operations, or processes described herein can be performed or implemented with one or more hardware or software modules, alone or in combination with other devices. In one embodiment, a software module is implemented with a computer program product including a computer-readable non-transitory medium containing computer program code, which can be executed by a computer processor for performing any or all of the steps, operations, or processes described.

Embodiments of the invention can also relate to a product that is produced by a computing process described herein. Such a product can include information resulting from a computing process, where the information is stored on a non-transitory, tangible computer readable storage medium and can include any embodiment of a computer program product or other data combination described herein.

The invention claimed is:

1. An assembly for performing a biological assay, the assembly comprising:
a first piece and a second piece operatively coupled to create a plurality of fluidic chambers, wherein the second piece comprises a first plurality of light pipes, the first plurality of light pipes capable of transmitting light between the plurality of fluidic chambers and a single sensing region.

2. The assembly of claim 1, the assembly further comprising a gasket located between the first piece and the second piece, the gasket operatively coupled to the first piece and the second piece to form fluid seals between the plurality of fluidic chambers.

3. The assembly of claim 2, wherein the gasket comprises thermoplastic elastomeric (TPE) overmolding.

4. The assembly of claim 1, wherein one or more components of the assembly are pre-dried to a residual moisture of at most 0.2% w/w.

5. The assembly of claim 1, wherein the first piece further comprises a plurality of coupling handles and the second piece further comprises a plurality of coupling latches, and wherein each of the plurality of coupling handles is configured to operatively couple with one of the plurality of coupling latches.

6. The assembly of claim 2, wherein a volume of the gasket is compressed by 5%-25% when the first piece and the second piece are operatively coupled.

7. The assembly of claim 1, wherein an outlet vent of each fluidic chamber of the plurality of fluidic chambers is sealed by a self-sealing vent material.

8. The assembly of claim 1, the assembly further comprising a hydrophobic membrane located between the first piece and the second piece, the hydrophobic membrane operatively coupled to the first piece and the second piece to form fluid seals.

9. The assembly of claim 8, wherein an outlet vent of each fluidic chamber of the plurality of fluidic chambers is sealed by the hydrophobic membrane.

10. The assembly of claim 8, wherein the hydrophobic membrane comprises polytetrafluoroethylene.

11. The assembly of claim 1, wherein at least one of the first piece and the second piece is injection molded.

12. The assembly of claim 1, wherein the second piece comprises a material selected from the group consisting of polymethlamethacrylate, polystyrene, polycarbonate, polypropylene, polyethylene, polyethylene terephthalate, cyclic olefin copolymer, polyamide, and combinations thereof.

13. The assembly of claim 1, wherein a volume of at least one of the plurality of fluidic chambers differs from a volume of at least one other of the plurality of fluidic chambers.

14. The assembly of claim 1, wherein a volume of each of the plurality of fluidic chambers is between 1 uL and 1000 uL.

15. The assembly of claim 1, wherein a volume of each of the plurality of fluidic chambers is on the order of 30 uL.

16. The assembly of claim 1, wherein at least one fluidic chamber of the plurality of fluidic chambers comprises dried or lyophilized reagents.

17. The assembly of claim 16, wherein the dried or lyophilized reagents comprise assay reagents.

18. The assembly of claim 17, wherein the assay reagents comprise a nucleic acid amplification enzyme and a DNA primer.

19. The assembly of claim 1, further comprising a circuit board comprising a microprocessor, the circuit board operatively coupled to the fluidic chambers.

20. The assembly of claim 19, wherein the circuit board further comprises a plurality of light emitting elements, each light emitting element capable of individually illuminating one of the plurality of fluidic chambers.

21. The assembly of claim 20, wherein the plurality of light emitting elements comprise LEDs.

22. The assembly of claim 20, wherein each light pipe of the first plurality of light pipes comprises at least one of one or more reflecting surfaces and one or more refracting surfaces configured to direct light between the plurality of fluidic chambers and the single sensing region.

23. The assembly of claim 20, wherein the second piece further comprises a transparent material forming a second plurality of light pipes, each second light pipe capable of transmitting light between one of the plurality of light emitting elements and one of the plurality of fluidic chambers.

24. The assembly of claim 23, wherein each light pipe of the second plurality of light pipes further comprises at least one of one or more reflecting surfaces and one or more refracting surfaces configured to direct light between one of the plurality of light emitting elements and one of the plurality of fluidic chambers.

25. The assembly of claim 20, wherein the microprocessor is programmed to cause each of the plurality of light emitting elements to emit light in a repeating pattern having a repetition frequency ranging from 0.01-100 Hz, wherein only one of the plurality of fluidic chambers is illuminated at any time.

26. The assembly of claim 25, wherein each of the plurality of the fluidic chambers is individually illuminated during each repetition of the pattern.

27. The assembly of claim 20, wherein the circuit board comprises a photosensor optically coupled to the signal sensing region.

28. The assembly of claim 27, wherein the photosensor comprises one of a CMOS chip, a photodiode, a phototransistor, a photocell, and a photomultiplier tube.

29. The assembly of claim 27, wherein the photosensor is configured to detect a color change.

30. The assembly of claim 27, wherein the photosensor is configured to detect an absorbance change.

31. The assembly of claim 19, wherein the circuit board further comprises a heating element comprising a ring shape, the heating element configured to heat the plurality of fluidic chambers.

32. The assembly of claim 31, further comprising a thermal pad comprising a ring shape, the thermal pad configured to transfer heat from the heating element to the plurality of fluidic chambers.

33. The assembly of claim 31, wherein the circuit board further comprises a temperature sensor.

34. The assembly of claim 19, wherein the circuit board further comprises an electronic result display mechanism.

35. The assembly of claim 27, wherein the microprocessor is programmed to analyze signals received from the photosensor.

36. The assembly of claim 31, wherein the microprocessor is programmed to regulate temperature using the heating element based on signals from the temperature sensor.

37. The assembly of claim 34, wherein the microprocessor is programmed to generate signals transmitted to the electronic result display mechanism.

38. The assembly of claim 1, wherein the biological assay is a diagnostic test.

39. The assembly of claim 1, wherein the plurality of fluidic chambers are radially-arranged around the single sensing region.

40. The assembly of claim 1, wherein the first plurality of light pipes are radially-arranged around the single sensing region.

41. The assembly of claim 1, wherein the single sensing region is located at or near a center of the second piece.

42. The assembly of claim 1, wherein a face of the first piece is radially-symmetric.

43. The assembly of claim 1, wherein a face of the second piece is radially-symmetric.

44. A method of determining one or more characteristics of a sample based on a modified optical property of the sample, the method comprising:
providing a reaction mixture to the plurality of fluidic chambers of the assembly of claim 1;
wherein the assembly further comprises:
a plurality of light emitting elements, each light emitting element capable of individually illuminating one of the plurality of fluidic chambers, and
a photosensor optically coupled to the single sensing region, and
wherein the reaction mixture comprises a biological sample, an optical property modifying reagent, and assay reagents;
generating a reaction using the biological sample and the assay reagents, the reaction generating a product;
reacting the product with the optical property modifying reagent, wherein the reacting is capable of modifying an optical property of the optical property modifying reagent to allow detection of the modified optical property indicative of the presence of a suspected analyte in the biological sample;
causing each of the plurality of light emitting elements to emit light; and
determining one or more characteristics of the sample using the photosensor based on the modified optical property.

45. The method of claim 44, wherein each light emitting element individually illuminates one of the plurality of fluidic chambers.

46. The method of claim 44, wherein each of the plurality of the fluidic chambers is individually illuminated during each repetition of the repeating pattern.

47. The method of claim 44, wherein the second piece of the assembly further comprises a transparent material forming a second plurality of light pipes, each second light pipe capable of transmitting light between one of the plurality of light emitting elements and one of the plurality of fluidic chambers, and wherein the light emitted by each of the plurality of light emitting elements is conveyed to the plurality of fluidic chambers through the second plurality of light pipes.

48. The method of claim 47, wherein the light emitted by each of the plurality of light emitting elements is conveyed to the plurality of fluidic chambers through the second plurality of light pipes using at least one of one or more reflecting surfaces and one or more refracting surfaces located within the second plurality of light pipes.

49. The method of claim 44, wherein the light emitted by each of the plurality of light emitting elements is conveyed to the photosensor through the first plurality of light pipes of the second piece.

50. The method of claim 49, wherein the light emitted by each of the plurality of light emitting elements is conveyed to the photosensor through the first plurality of light pipes using at least one of one or more reflecting surfaces and one or more refracting surfaces located within the first plurality of light pipes.

51. The method of claim 44, wherein causing each of the plurality of light emitting elements to emit light in the repeating pattern further comprises causing each of the plurality of light emitting elements to emit light at a different and distinct time such that only one of the plurality of fluidic chambers is illuminated at any time.

52. The method of claim 44, wherein generating the reaction comprises heating the reaction mixture with a heating element based on signals transmitted from a microprocessor to the heating element.

53. The method of claim 44, wherein determining one or more characteristics of the sample using the photosensor further comprises a microprocessor analyzing signals received from the photosensor.

54. The method of claim 44, further comprising receiving signals from a temperature sensor of the assembly and analyzing the signals received from the temperature sensor using a microprocessor.

55. The method of claim 44, further comprising displaying the determined characteristics on an electronic result display mechanism of the assembly by transmitting signals generated by a microprocessor to the electronic result display mechanism.

56. The method of claim 44, wherein causing each of the plurality of light emitting elements to emit light further comprises causing each of the plurality of light emitting elements to emit light in a repeating pattern at a repetition frequency between 0.01-100 Hz.

57. The method of claim 44, wherein determining one or more characteristics of the sample using the photosensor further comprises detecting a color change of the sample using the photosensor.

58. The method of claim 44, wherein determining one or more characteristics of the sample using the photosensor further comprises detecting an absorbance change of the sample using the photosensor.

59. The method of claim 44, wherein the optical property modifying reagent solution comprises a liquid buffer.

60. The method of claim 44, wherein the assay reagents comprise a nucleic acid amplification enzyme and a DNA primer.

61. The method of claim 44, wherein the assay reagents are dried or lyophilized.

62. The assembly of claim 1, wherein the first piece and the second piece are operatively coupled by one or more of an adhesive, ultrasonic welding, and laser welding.

63. The assembly of claim 1, wherein each fluidic chamber is substantially equidistant from the single sensing region.

64. The assembly of claim 1, wherein each first light pipe is capable of transmitting light between one of the plurality of fluidic chambers and the single sensing region.

* * * * *